United States Patent
Mougin

(10) Patent No.: US 7,632,873 B2
(45) Date of Patent: Dec. 15, 2009

(54) COSMETIC DERMATOLOGICAL COMPOSITION COMPRISING AT LEAST ONE GRADIENT COPOLYMER, MAKEUP COMPRISING THE COSMETIC OR DERMATOLOGICAL COMPOSITION AND COSMETIC METHOD USING THE COMPOSITION

(75) Inventor: Nathaie Mougin, Paris (FR)

(73) Assignee: L'Oreal S.A., Paris (FR)

( * ) Notice: Subject to any disclaimer, the term of this patent is extended or adjusted under 35 U.S.C. 154(b) by 904 days.

(21) Appl. No.: 10/734,301

(22) Filed: Dec. 15, 2003

(65) Prior Publication Data

US 2004/0191199 A1 Sep. 30, 2004
US 2005/0255068 A9 Nov. 17, 2005

Related U.S. Application Data

(60) Provisional application No. 60/457,998, filed on Mar. 28, 2003.

(30) Foreign Application Priority Data

Dec. 13, 2002 (FR) .................................. 02 15858

(51) Int. Cl.
*A61K 47/00* (2006.01)

(52) U.S. Cl. .......................... 514/937; 424/401; 424/61; 424/78.03

(58) Field of Classification Search ................. 424/401, 424/61, 78.03; 514/937
See application file for complete search history.

(56) References Cited

U.S. PATENT DOCUMENTS

| 5,807,937 | A | | 9/1998 | Matyjaszewski et al. |
| 6,113,930 | A | * | 9/2000 | Mondet et al. .............. 424/401 |
| 6,312,672 | B1 | | 11/2001 | Coolbaugh et al. |

OTHER PUBLICATIONS

Gagliardi et al., 1967, CAS: 66:66679.*
M. Kryszewski, "Gradient Polymers and Copolymers," Polymers for Advanced Technologies, vol. 9, No. 4, Apr. 1, 1998, pp. 244-259.

* cited by examiner

*Primary Examiner*—Rei-tsang Shiao
(74) *Attorney, Agent, or Firm*—Finnegan, Henderson, Farabow, Garrett & Dunner LLP

(57) ABSTRACT

A cosmetic or dermatological composition comprising at least one gradient copolymer comprising at least two different monomers, displaying a mass polydispersity index (Ip) less than or equal to 2.5 and for example, additionally a low composition polydispersity. A cosmetic or dermatological method for make-up or care of keratinous substances, notably the skin of the body or of the face, the nails, the hair and/or the eyelashes, comprising application of a cosmetic composition as defined above on the said substances.

80 Claims, 7 Drawing Sheets

# 10% methacrylic acid initially:

COPOLYMER WITH A VERY LOW GRADIENT, FOR WHICH NANOSTRUCTURIZATION CANNOT BE EXPECTED.

# 20% methacrylic acid initially:

COPOLYMER WITH A HYDROPHILIC "HEAD" AND HYDROPHOBIC "TAIL," WITH A GRADIENT THAT IS SUFFICIENTLY PRONOUNCED TO LEAD TO NANOSTRUCTURIZATION.

# 50% methacrylic acid initially:

SINCE THE MONOMERS ARE ISOREACTIVE IN THESE CONDITIONS, THE COPOLYMER OBTAINED IS OF THE ALTERNATING TYPE.

FIG. 2

COSMETIC DERMATOLOGICAL COMPOSITION COMPRISING AT LEAST ONE GRADIENT COPOLYMER, MAKEUP COMPRISING THE COSMETIC OR DERMATOLOGICAL COMPOSITION AND COSMETIC METHOD USING THE COMPOSITION

This application claims benefit of U.S. Provisional Application No. 60/457,998, filed Mar. 28, 2003.

This disclosure relates to novel topical cosmetic or dermatological compositions comprising at least one gradient copolymer comprising at least two monomeric residues, such as amphiphilic gradient copolymers, that may, for example, be soluble or dispersible in water and/or in organic solvents, and wherein the at least one gradient copolymer exhibits a mass polydispersity index (Ip) less then or equal to 2.5.

In the area of cosmetics, we often aim to provide compositions that make it possible to obtain a deposit that is notably adhesive or film-forming, on the keratinous substances in question, such as the hair, skin, eyelashes or nails.

For example, these compositions can supply colour (make-up or hair colouring compositions), gloss or matt appearance (compositions for skin care or make-up), physical properties, such as for shaping (hair-care compositions, for instance, for styling), and properties of care or protection (care compositions, for example, for moisturizing or for UV protection).

Generally, cosmetic compositions call for such characteristics as good retentiveness and long-lasting quality of the cosmetic deposit, as well as good adhesion to the substrate. For example, it may be useful for the deposit to be able to withstand mechanical action, such as rubbing, transfer by contact with another object; resistance to water, sweat, tears, rain, sebum and oils. This may be true, for instance, in the case of make-up, such as in the area of lipsticks where the colour and gloss are required to be long-lasting and there should be no transfer of colour; and in the area of foundations, eyeshadows and powders, where the colour supplied is to be long-lasting, while maintaining the matt appearance of the initial complexion for as long as possible despite the secretion of sebum and sweat, as well as non-transfer. Furthermore, make-up compositions should be comfortable to wear and their texture should not be too sticky.

To reconcile some of these varying properties within a single composition, we generally use a mixture of several polymers, with very different chemical natures, each polymer supplying one of the desired characteristics. However, the use of a mixture of polymers which possess different chemical natures may, for example, not be compatible, and can cause problems of demixing within the composition.

The use of random polymers, for example conventional acrylic polymers obtained by classical radical polymerization and by random mixing of monomers, does not provide a satisfactory solution to these problems. In fact, the random polymers, known in the prior art, exhibit a dispersity in composition of the polymer chains, which may also lead to demixing of the polymers within the formulation.

This disclosure overcomes at least one drawback of the prior art by proposing, as recited in the claims herein, a cosmetic or dermatological composition comprising at least one gradient copolymer, of the type that can avoid the problems of demixing within the formulation, while providing at least one desired cosmetic property.

BRIEF DESCRIPTION OF THE DRAWINGS

FIG. 2 shows a schematic representation of different polymers obtained from a styrene/methacrylic acid gradient copolymer.

Figure 1:
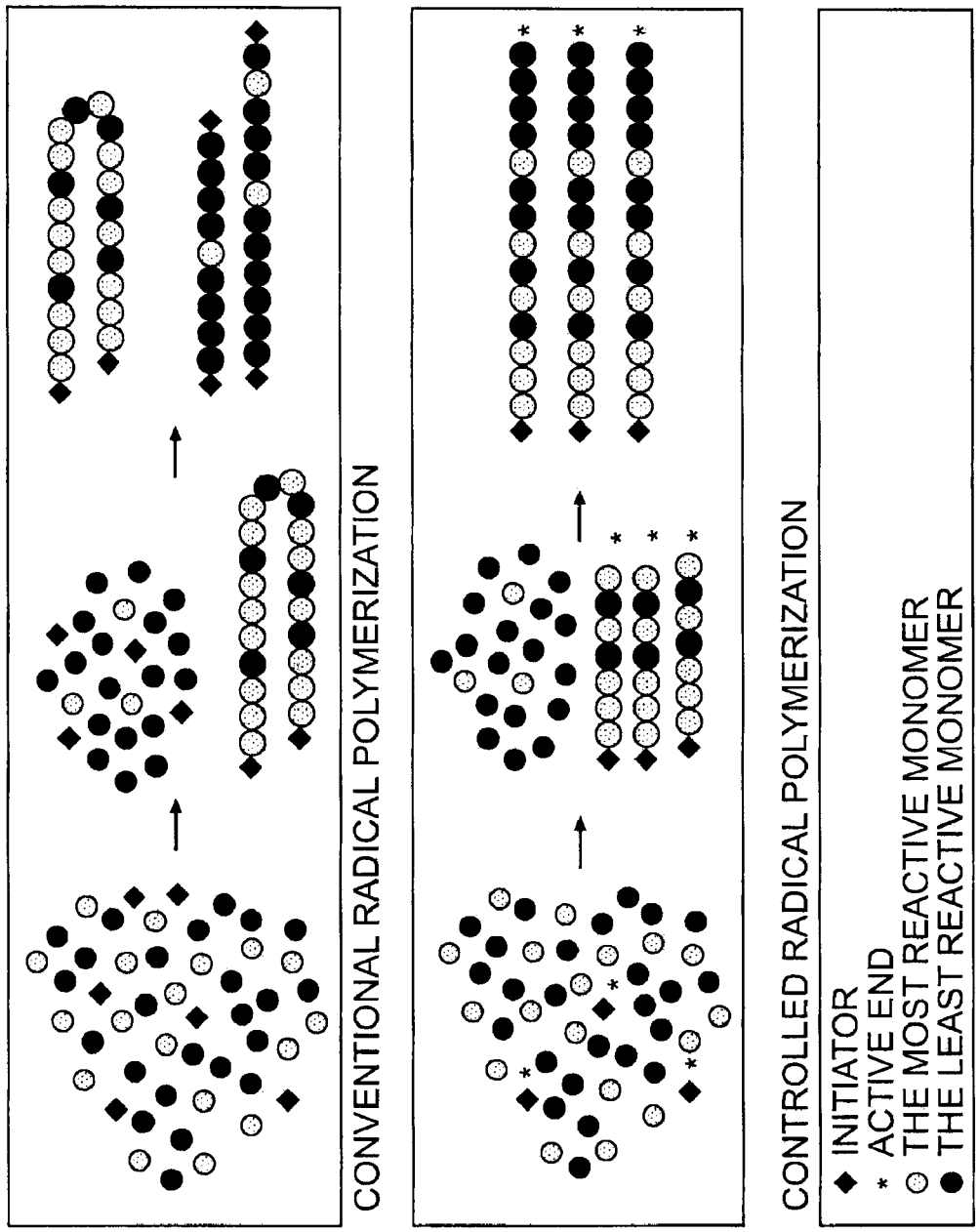
FIG. 1 shows a random polymer obtained by classical radical polymerization of two monomers, and a gradient copolymer.

One aspect of the present disclosure is a cosmetic or dermatological composition comprising at least one gradient copolymer comprising at least two different monomeric residues, and displaying a mass polydispersity index (Ip) less than or equal to 2.5, ranging from 1.1 to 2.3, for example, ranging from 1.15 to 2.0, and further, for example, ranging from 1.2 to 1.9 or even to 1.8.

The at least one gradient copolymer, as disclosed herein, can have a low dispersity in composition and the polymer chains comprising the gradient copolymers can have similar or the same structures. Therefore, such copolymers are compatible with one another and, as a result, the cosmetic compositions comprising these copolymers exhibit less than all of the drawbacks and limitations of the compositions of the prior art.

For example, the at least one gradient copolymer, as disclosed herein, can be easily manipulated in water or in an organic solvent medium, while retaining its useful rheological properties.

Furthermore, the at least one copolymers, disclosed herein, can be chosen from gradient copolymers, which comprise at least two different monomeric residues, and which may have a low mass polydispersity, as defined in paragraph [009], and, for instance, a low composition polydispersity.

The mass polydispersity can be illustrated using the mass polydispersity index (Ip) of the copolymer, which is equal to the ratio of the weight-average molecular weight (Mw) to the number-average molecular weight (Mn).

A low mass dispersity reflects approximately identical chain lengths, which is the case for the gradient copolymers as disclosed herein.

According to the disclosure, the at least one gradient copolymer has a mass polydispersity index less than or equal to 2.5, for example, ranging from 1.1 to 2.3, for instance, ranging from 1.15 to 2.0, or further, for example, from 1.2 to 1.9 or 1.8.

Furthermore, the weight-average molecular weight of the at least one gradient copolymer can range from 5,000 g/mol to 1,000,000 g/mol, for instance, range from 5,500 g/mol to 800,000 g/mol, and further, for example, from 6,000 g/mol to 500,000 g/mol.

The number-average molecular weight of the at least one gradient copolymer can also range from 5,000 g/mol and 1,000,000 g/mol, for example, from 5,500 g/mol and 800,000 g/mol, and even further, for example, from 6,000 g/mol and 500,000 g/mol.

The weight-average (Mw) and number-average (Mn) molecular weights are determined by gel permeation liquid chromatography ("GPC") (wherein eluent THF, a calibration curve established with linear polystyrene standards, and refractometric detector are used).

The at least one gradient copolymer, according to the present disclosure, could, for example, also have a low composition dispersity. For the purpose of this disclosure, low composition dispersity means that all the polymer chains of the at least one gradient copolymer, have a roughly similar composition (i.e. a concatenation of monomers) and are therefore generally homogeneous in composition.

In order to show that all the polymer chains of the at least one gradient copolymer have a similar composition, liquid adsorption chromatography ("LAC") can be used to separate the chains of the copolymers according to their polarity, rather than according to their molecular weight. Without being bound by theory, it is believed that the chain's polarity reflects the chemical composition of the polymers of which the material is constituted.

One may refer to the publication Macromolecules (2001), 34, 2667, which describes the LAC technique.

For instance, the composition polydispersity can be defined from the LAC curve (the curve representing the proportion of polymers as a function of the elution volume): if we call the minimum value of the elution volume at mid-height of the curve $V^{1/2}$ min, and the maximum value of the elution volume at mid-height of the curve $V^{1/2}$ max, the composition polydispersity is regarded as low if the difference ($V^{1/2}$max–$V^{1/2}$min) is less than or equal to 3.5, for example, ranging from 1 to 2.8 and further, ranging from 1.2 to 2.5.

The LAC curve can be further defined by a Gaussian curve with the formula:

$$y = \frac{A}{w\sqrt{\frac{\pi}{2}}} \times e^{-2\frac{(x-x_0)^2}{w^2}} + y_o$$

wherein:
$x_0$ is the value of x (elution volume) at the centre of the peak
w is equal to twice the standard deviation of the Gaussian distribution (i.e. $2\sigma$) or corresponds approximately to 0.849 times the width of the peak at mid-height
A is equal to the area under the peak
$y_0$ is the value of y corresponding to $x_0$.

The composition dispersity can also be defined by the value of w as defined above.

For example, the composition dispersity can be wherein w ranges from 1 to 3, for instance, ranges from 1.1 to 2.3 and further from 1.1 to 2.0.

The at least one gradient copolymer, as disclosed herein, can be obtained by living or pseudo-living polymerization.

It is known that living polymerization is a polymerization for which the growth of the polymer chains only ceases with the disappearance of the monomer. The number-average molecular weight (Mn) increases with the degree of conversion. Anionic polymerization is a typical example of living polymerization. Such polymerizations result in copolymers with low mass dispersity, i.e. polymers with a mass polydispersity index (Ip) generally less than 2.

As for pseudo-living polymerization, it is associated with controlled radical polymerization. Among the main types of controlled radical polymerization, non-limiting mention may be made of:

radical polymerization controlled by nitroxides. Reference may be made, for example to Patent Applications Nos. WO 96/24620 and WO 00/71501, which describe the tools for this polymerization and their use, as well as to the articles published by Fischer (Chemical Reviews, 2001, 101, 3581), by Tordo and Gnanou (J. Am. Chem. Soc. 2000, 122, 5929) and Hawker (J. Am. Chem. Soc. 1999, 121, 3904);

atom transfer radical polymerization, for instance, as described in Patent Application No. WO 96/30421, which takes place by reversible insertion on an organometallic complex in a carbon-halogen bond; and radical polymerization controlled by sulphur derivatives of the xanthate type, dithioesters, trithiocarbonates or carbamates, as described in Patent Applications Nos. FR 2821620, WO 98/01478, WO 99/35177, WO 98/58974, WO 99/31144, WO 97/01478 and in the article by Rizzardo et al. (Macromolecules, 1998, 31, 5559).

Controlled radical polymerization denotes polymerizations for which the secondary reactions that usually lead to the disappearance of the propagating species (termination or transfer reaction) are made to become very unlikely, relative to the propagation reaction, owing to the action of a free radical controlling agent. The drawback of this form of polymerization can be that when the concentrations of free radicals become large in relation to the concentration of monomer, the secondary reactions become determining again and tend to broaden the mass distribution.

In these forms of polymerization, the polymer chains of the at least one gradient copolymer, disclosed herein, grow simultaneously and therefore usually incorporate the same ratios of comonomers at any given moment. All the chains, therefore, can have the same or similar structures, which can result in low composition dispersity. These chains also have a low mass polydispersity index.

Gradient copolymers are copolymers wherein the ratio of the various monomers varies along the length of the chain. The distribution in the polymer chains of the comonomers depends on the variation of the relative concentrations of the comonomers during synthesis.

The at least one gradient copolymer, according to the present disclosure, can include at least two different monomers, whose concentration along the polymer chain changes gradually, in a regular and predictable manner.

Accordingly, all the polymer chains have at least one monomer Mi, wherein, regardless of the normalized position x on the polymer chain, the probability of finding this monomer Mi along the length of the chain is not zero.

One of the characteristics by which gradient copolymers can be defined is that at any moment in the polymerization, all the chains are subject to the presence of all of the monomers. Thus, in the reaction medium, the concentration of each monomer is always non-zero, at any given moment in the polymerization.

This distinguishes the gradient copolymers, as disclosed herein, from the usual block polymers, wherein the variation of the monomers along the polymer chain is not regular. For example for a diblock copolymer AB, within the block A, the concentration of the other monomer B is always zero.

In the case of random polymers, the variation of the monomers along the polymer chain will normally not be gradual, regular and predictable.

As shown in FIG. 1, for illustration purposes, a random polymer obtained by classical radical polymerization of two monomers will differ from a gradient copolymer in the distribution of the monomers, in that a random polymer is normally not identical on all the chains, nor in the length of the said chains, which is normally not identical for all the chains.

For a theoretical description of gradient copolymers, reference may be made to the following works:

T. Pakula et al., Macromol. Theory Simul. 5, 987-1006 (1996);
A. Aksimetiev et al., J. of Chem. Physics 111, No. 5;
M. Janco, J. Polym. Sci., Part A: Polym. Chem. (2000), 38(15), 2767-2778;
M. Zaremski et al., Macromolecules (2000), 33(12), 4365-4372;
K. Matyjaszewski et al., J. Phys. Org. Chem. (2000), 13(12), 775-786;
Gray, Polym. Prepr. (Am. Chem. Soc., Div. Polym. Chem.) (2001), 42(2), 337-338;
K. Matyjaszewski, Chem. Rev. (Washington, D.C.) (2001), 101(9), 2921-2990.

Among gradient copolymers, a distinction may be made between natural gradient copolymers and artificial gradient copolymers.

A natural gradient copolymer is a gradient copolymer obtained by batch synthesis from an initial mixture of the comonomers. The distribution of the various monomers in the chain follows a pattern that can be deduced from the relative reactivity and the initial concentrations of the monomers. These copolymers constitute the simplest class of gradient copolymers as it is the initial mixture that determines the final properties of the product.

An artificial gradient copolymer is a gradient copolymer for which the concentration of monomers is varied, by a special measure, during synthesis. In the case of artificial gradient copolymers, there is a shift from one mixture of monomers to another in the chain owing to a sudden, abrupt change of the monomers in the reaction medium (for instance, stripping of the first mixture or addition of at least one new monomer). There may even be a substantial disappearance of at least one of the monomers to the benefit of at least one other monomer.

The gradient is characterized experimentally by measuring the chemical composition of the polymer during polymerization. Measurement is taken, indirectly, by determining the variation in the content of the different monomers at any given moment. This can be done using NMR and UV, for example.

In general, for polymers prepared by living or pseudo-living polymerization, chain length is related linearly to the degree of conversion.

By taking a sample of the polymerization solution, at different moments in the polymerization, and then measuring the difference in the content of each monomer, one can arrive at the composition of the gradient.

In a gradient polymer, generally, the compositions of the chains have a narrow distribution. For instance, there is no overlap between the peak of the gradient copolymer and those of the respective homopolymers, which shows that the material obtained in gradient conditions is made up of polymer chains of identical composition. In contrast, in classical random polymerization, different kinds of chains can normally coexist, including those of the respective homopolymers.

It is possible to characterize gradient copolymers by a vector that is characteristic of each copolymer.

In fact, since it is assumed that there is an infinite number of polymers characterized by a given chemical composition, it is possible to define a polymer by describing the distribution of the monomers along the chain. This involves a description with several variables. This vector is a point in space of the chemical compositions.

The more precise definition is that G is a vector whose coordinates are the concentrations of the monomers along the polymer chain. These concentrations are defined by the rules of the reactivity coefficients of each monomer, and are therefore related to the concentration of the free monomers during synthesis: from the moment when the monomer is not at zero concentration in the reaction mixture, it is not at zero concentration in the polymer.

It is therefore possible to characterize gradient copolymers by the function G(x), which defines the composition gradient:

$$\vec{G}(x) = \Sigma \overrightarrow{[M_i](x)}$$

wherein:

x denotes a normalized position on the polymer chain, and
[Mi](x) is the relative concentration, at the position x, of the monomer Mi, expressed in mol%.

The function G(x) therefore describes the composition of the gradient copolymer locally. Two different copolymers can have an equivalent overall composition but very different local distributions of the monomers, and therefore different gradients.

For example, in the case of a diblock copolymer AB (50/50), function [A] has a value of 1 up to $x \leq 1/2$ and 0 thereafter.

The factors that can determine the gradient, include: the relative reactivity coefficients of each monomer (called $r_i$ for the monomer Mi), which mainly depend on the type of synthesis process employed (e.g., homogeneous, dispersed) and on the solvents employed, the initial concentrations of each of the monomers, and any additions of monomers in the course of polymerization.

Thus, for example, let us consider a gradient copolymer of styrene (M1) with a relative reactivity coefficient $r_1 = 0.418$ and of methacrylic acid (M2), with $r_2 = 0.6$, in a system of homogeneous polymerization.

By varying the initial concentrations of styrene and methacrylic acid, different gradient copolymers can be obtained, each having chains with entirely different structures.

When the initial concentration of methacrylic acid is 10% by weight, one can obtain a copolymer of very low gradient, for which nanostructurization cannot be expected. When the initial concentration is 20% by weight, one can obtain a gradient copolymer with a hydrophilic "head" and a hydrophobic "tail," with a gradient that is sufficiently pronounced to lead to nanostructurization. When the concentration is 50% by weight, the monomers can be isoreactive in these conditions, and therefore, the copolymer obtained is of the alternating type.

Although the copolymers described are all gradient copolymers of styrene and methacrylic acid, the difference in the initial concentration of the monomers leads to chains with completely different structures, conferring on the copolymers different properties. This example therefore illustrates the influence of the initial monomer compositions on the arrangement of the various monomers along the chain.

In the case of a styrene/methacrylic acid gradient copolymer, the different polymers obtained can be represented schematically as demonstrated in FIG. 2, with the white units corresponding to styrene and the dark units corresponding to methacrylic acid.

The structure of the polymers shown in FIG. 2 may be determined by the disappearance of the methacrylic acid as a function of the degree of conversion.

The at least one gradient copolymer, as disclosed herein, comprises at least two different monomeric residues, wherein each of which can be present in a proportion of 1% to 99% by weight, relative to the total weight of the copolymer, especially in an amount ranging from 2% to 98% by weight, relative to the total weight of the copolymer, and for instance, in an amount ranging from 5% to 95% by weight, relative to the total weight of the copolymer.

For example, the at least one gradient copolymer comprises at least one monomeric residue resulting from at least one monomer chosen from hydrophilic monomers.

These hydrophilic monomeric residues can be present in an amount ranging from 1% to 99% by weight, relative to the total weight of the copolymer, for example, in an amount ranging from 2% to 70% by weight, relative to the total weight of the copolymer, further for example, in an amount ranging from 5% to 50% by weight, relative to the total weight of the copolymer, or even further, ranging from 10% to 30% by weight, relative to the total weight of the copolymer.

For purposes of the present disclosure, "hydrophilic monomer" designates monomers of which the homopolymers are soluble or dispersible in water, or of which an ionic form is soluble or dispersible in water.

A homopolymer is called water-soluble if it forms a clear solution when it is in solution at 1% by weight in water, at 25° C.

A homopolymer is called water-dispersible if, at 1% by weight in water, at 25° C., it forms a stable suspension of fine, generally spherical, particles. The average size of the particles making up the said dispersion can be less than 1 μm and, more generally, can ranges from 5 to 400 nm, such as from 10 to 250 nm. These particle sizes are measured by light scattering.

For example, the hydrophilic monomer can possibly have a Tg less than or equal to 20° C., but more generally can have a Tg greater than or equal to 20° C., such as greater than or equal to 50° C.

The gradient copolymer can also comprise at least one hydrophobic monomeric residue, for example, resulting from a hydrophobic monomer that can be made hydrophilic after polymerization, or a mixture of such monomers. The at least one hydrophobic monomer can be made hydrophilic, for example, by chemical reaction, such as hydrolysis, by chemical modification, such as modification of an ester functional group, or by incorporation of chains that have a hydrophilic unit, for example of the carboxylic acid type.

These hydrophobic monomers can be present in an amount ranging from 1% to 99% by weight, relative to the total weight of the copolymer, for example, in an amount ranging from 30% to 98% by weight, relative to the total weight of the copolymer, for instance, ranging from 50% to 95% by weight, relative to the total weight of the copolymer, or such as in an amount ranging from 70% to 90% by weight, relative to the total weight of the copolymer.

For example, the hydrophobic monomers that can be made hydrophilic can be present in an amount ranging from 1% to 99% by weight, relative to the total weight of the copolymer, such as in an amount ranging from 5% to 50% by weight, relative to the total weight of the copolymer, and further, for example, in an amount ranging from 8% to 25% by weight, relative to the total weight of the copolymer.

For example, the hydrophobic monomer may possibly have a Tg less than or equal to 20° C., but more generally can have a Tg greater than or equal to 20° C., such as greater than or equal to 30° C.

For example, the gradient copolymer, disclosed herein, comprises at least one monomeric residue resulting from a monomer having a Tg less than or equal to 20° C., ranging from −150° C. to 20° C., such as ranging from −130° C. to 18° C., and further, ranging from −120° C. to 15° C., or a mixture of such monomers, which may be identical or different.

The monomers with Tg less than or equal to 20° C. can be present in an amount ranging from 1% to 99% by weight, relative to the total weight of the copolymer, such as in an amount ranging from 10 to 90% by weight, relative to the total weigh of the copolymer, for example, in an amount ranging from 20% to 80% by weight, relative to the total weight of the copolymer, or for instance, in an amount ranging from 50% to 75% by weight, relative to the total weight of the copolymer.

The monomers with Tg greater than or equal to 20° C. can therefore be present in an amount ranging from 1% to 99% by weight, relative to the total weigh of the copolymer, such as in an amount ranging from 10% to 90% by weight, relative to the total weight of the copolymer, such as in an amount ranging from 20% to 80% by weight, relative to the total weight of the copolymer, or for instance, in an amount ranging from 25% to 50% by weight, relative to the total weight of the copolymer.

For purposes of the present disclosure, "Tg monomer" designates monomers which can create homopolymers with such a Tg, measured by the method described hereinbelow.

As disclosed herein, the Tg (or glass transition temperature) is measured in accordance with standard ASTM D3418-97, by differential scanning calorimetry (DSC) in a calorimeter, over a temperature range from −100° C. to +150° C. at a heating rate of 10° C./min in 150-μl aluminium crucibles.

In one aspect of the disclosure, the at least one gradient copolymer, as disclosed herein, comprises three different monomeric residues, wherein each monomeric residue can be present in an amount ranging from 5% to 90% by weight, relative to the total weight of the copolymer, such as in an amount ranging from 7% to 86% by weight, relative to the total weight of the copolymer.

For example, the gradient copolymer can comprise from 5% to 25% by weight of a first monomer, from 5% to 25% by weight of a second monomer and from 50% to 90% by weight of a third monomer.

For further example, the at least one gradient copolymer, as disclosed herein, can comprise a hydrophilic monomer from 5% to 25% by weight, relative to the total weight of the copolymer, a monomer with Tg less than or equal to 20° C. from 50% to 90% by weight, relative to the total weight of the copolymer and an additional monomer from 5% to 25% by weight, relative to the total weight of the copolymer.

The hydrophilic monomers, according to the present disclosure, can be chosen from:
  derivatives of $C_1$-$C_6$ aminoalkyl (meth)acrylates, for example, N, N-di(C1-C4) alkylamino($C_1$-$C_6$)alkyl (meth)acrylates, such as N,N-dimethylaminoethyl methacrylate (MADAME) and N,N-diethylaminoethyl methacrylate (DEAMEA);
  $C_1$-$C_4$ N,N-dialkyl(meth)acrylamides and $C_1$-$C_4$N,N-dialkyl$C_1$-$C_6$aminoalkyl(meth)acrylamides, such as N,N-dimethylacrylamide, N,N-dimethylaminopropylacrylamide (DMAPA) and N,N-dimethylaminopropylmethacrylamide (DMAPMA),
  $C_1$-$C_8$ dialkyldiallylamines, such as dimethyidiallylamine;
  vinylamines;
  vinylpyridines, for example, 2-vinylpyridine and 4-vinylpyridine;
  and the acid salts thereof and quaternized forms thereof.
Among the inorganic acids that may be used, non-limiting mention may be made of sulphuric acid, hydrochloric acid, hydrobromic acid, hydriodic acid, phosphoric acid, boric acid.

Among the organic acids that may be used, non-limiting mention may be made of acids comprising at least one group chosen from carboxylic, sulphonic and phosphonic groups. The organic acids may be chosen from linear, branched, cyclic aliphatic acids, and aromatic acids. These acids can also comprise at least one heteroatom chosen from O and N, for example in the form of hydroxyl groups. Non-limiting mention may also be made of acids chosen from propionic, acetic, terephthalic, citric and tartaric acids.

Non-limiting examples of quaternizing agents can be chosen from alkyl halides, such as methyl bromide and alkyl sulphates, such as methyl sulphate and propane sultone.

In regard to the at least one hydrophilic monomer, non-limiting mention may also be made of:
  carboxylic acids, for instance monocarboxylic and dicarboxylic acids, and further for instance, ethylenic acids, and even further for instance acrylic acids, methacrylic acids, crotonic acids, itaconic acids, fumaric acids, and maleic acids;
  carboxylic anhydrides comprising a vinyl bond, such as maleic anhydride;
  ethylenic sulphonic acids, such as styrenesulphonic acids, acrylamidopropanesulphonic acids, and their salts;
  vinylbenzoic acids, vinylphosphonic acids, and their salts;
  the potassium salts of acryloyloxy-3-sulphopropyl, and the compounds of formula $CH_2=CHCOOCH_2OCH_2(OH)CH_2SO_3^-Na^+$. 

The neutralizing agent may be chosen from inorganic bases, such as LiOH, NaOH, KOH, Ca(OH)$_2$, and NH$_4$OH; and may be chosen from organic bases, for example, primary, secondary and tertiary amines, such as alkylamines, optionally hydroxylated, such as dibutylamines, triethylamines, stearamines, and alternatively 1-amino-2-methyl-2-propanols, monoethanolamines, diethanolamines, stearamidopropyldimethylamines.

Non-limiting mention may further be made of the following hydrophilic monomers:
  amides of unsaturated carboxylic acids, for instance acrylamides, methacrylamides, and their N-substituted derivatives, such as C$_1$-C$_4$ N-alkyl(meth)acrylamides, such as N-methylacrylamide; C$_1$-C$_4$ N,N-dialkyl(meth)acrylamides, such as N,N-dimethylacrylamide;
  hydroxyalkyl (meth)acrylates, such as those comprising alkyl groups comprising from 2 to 4 carbon atoms, for example, hydroxyethyl (meth)acrylates;
  (meth)acrylates of polyethylene glycol (5 to 100 EO) and of glycol, optionally substituted on their terminal function by a group chosen from alkyl, phosphate, phosphonate and sulphonate groups, for example glycerol acrylates, methoxypolyethylene glycol (meth)acrylates (8 and 12 OE); and hydroxypolyethylene glycols (meth) acrylate;
  alkoxyalkyl (meth)acrylates, such as ethoxyethyl (meth) acrylate;
  (meth)acrylates of polysaccharides, such as sucrose acrylates;
  vinylamides, such as vinylacetamide; which may optionally be cyclic, for instance vinyl lactams, such as N-vinylpyrrolidone and N-vinylcaprolactam;
  vinyl ethers, such as vinyl methyl ether.

Additionally, non-limiting mention may further be made of the following hydrophilic monomers:
  methacrylamidopropoxytrimethylammoniumbetaines;
  N,N-dimethyl-N-methacryloxyethyl-N-(3-sulphopropyl) ammoniumbetaines,
  3-methacryloylethoxycarbonylpyrid iniums a compound of formula:

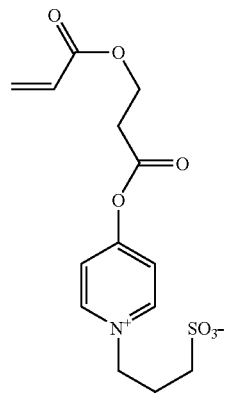

4-vinylpyridiniumsulphopropylbetaine of formula:

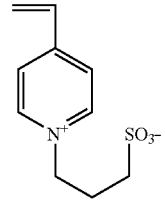

Also, in one aspect of the disclosure, the hydrophilic monomers are chosen from- N,N-dimethylaminoethyl methacrylates (MADAME), acrylic acids, methacrylic acids, crotonic acids, styrenesulphonic acids, acrylamidopropanesulphonic acids, dimethylaminopropylmethacrylamides (DMAPMA), styrene sulphonates, hydroxyethyl acrylates, glycerol acrylates, ethoxyethyl methacrylates, ethoxyethyl acrylates, methoxypolyethylene glycols (meth)acrylate (8 and 12 EO), hydroxypolyethylene glycol (meth)acrylates, N-vinylpyrrolidones, N-vinylcaprolactams, acrylamides, N,N-dimethylacrylamides.

Among the examples of hydrophobic monomers that can be made hydrophilic, such as by hydrolysis, non-limiting mention may be made of C$_1$-C$_4$ alkyl (meth)acrylates, such as teit-butyl (meth)acrylates and ethyl (meth)acrylates, which can lead to (meth)acrylic acid being obtained via hydrolysis.

Among the examples of monomers that can form a homopolymer with a Tg less than or equal to 20° C. which may be hydrophilic, as disclosed herein, non-limiting mention may be made of:
  ethylenic hydrocarbons comprising from 2 to 10 carbons, such as ethylene, isoprene, and butadiene;
  acrylates with the formula $CH_2=CHCOOR_1$, wherein R$_1$ is chosen from saturated and unsaturated, linear and branched, hydrocarbon groups, comprising from 1 to 12 carbons, with the exception of the tert-butyl group, and optionally comprising at least one heteroatom chosen from O, N, S, and Si, wherein the alkyl groups may optionally be substituted by at least one substituent selected from hydroxyl group and halogen atoms (such as Cl, Br, I and F);
  non-limiting examples of groups R$_1$ may be chosen from are methyl, ethyl, propyl, butyl, isobutyl, hexyl, ethylhexyl, octyl, lauryl, isooctyl, isodecyl, hydroxyethyl, hydroxypropyl, methoxyethyl, ethoxyethyl, methoxypropyl and ethylperfluorooctyl groups, and propylpolydimethylsiloxanes;

$R_1$ can also be chosen from groups of formula —(R")x-$(OC_2H_4)_n$—OR', wherein x is an integer chosen from 0 and 1, R" is chosen from saturated and unsaturated, linear and branched, hydrocarbon groups, comprising from 1 to 12 carbons, n is an integer chosen from 5 to 100 and R' is chosen from H and $CH_3$; such as methoxy(POE)8-stearyl groups;

methacrylates of formula: $CH_2$=$C(CH_3)$—$COOR_2$, wherein $R_2$ is chosen from saturated and unsaturated, linear and branched, hydrocarbon groups, comprising from 3 to 12 carbons, and may optionally comprise at least one heteroatom chosen from O, N, S and Si, wherein the alkyl group may optionally be substituted with at least one substituent chosen from hydroxyl group and halogen atoms (such as Cl, Br, I, F); non-limiting examples of groups $R_2$ may be chosen from are hexyl, ethylhexyl, octyl, lauryl, isooctyl, isodecyl, dodecyl, methoxyethyl, methoxypropyl, ethoxyethyl; ethylperfluorooctyl, and propylpolydimethylsiloxane groups; $R_2$ can also be chosen from groups of formula —(R")x-$(OC_2H_4)_n$—OR ', wherein x is an integer chosen from 0 and 1, R" is chosen from saturated and unsaturated, linear and branched, hydrocarbon groups, comprising from 1 to 12 carbons, n is an integer chosen from 5 to 100 and R' is chosen from H and $CH_3$; such as methoxy(POE)8-stearyl groups;

N- and N,N-substituted derivatives of amides of $C_{1-12}$ unsaturated carboxylic acids, for instance $C_{1-12}$ N-alkyl (meth)acrylamides, such as N-octylacrylamide;

vinyl esters of formula: $R_3$—CO—O—CH=$CH_2$ wherein $R_3$ is chosen from linear and branched alkyl groups comprising from 2 to 12 carbons, and examples of such vinyl esters include vinyl propionate, vinyl butyrate, vinyl ethylhexanoate, vinyl neononanoate, and vinyl neododecanoate;

vinyl alkyl ethers comprising from 1 to 12 carbons, such as vinyl methyl ether, and vinyl ethyl ether.

Additionally, the monomers with Tg less than or equal to 20° C. may be chosen from:

isoprene and butadiene;

methyl, ethyl, isobutyl, n-butyl, ethylhexyl, methoxyethyl, ethoxyethyl and hydroxypolyethylene glycol acrylates;

ethoxyethyl, hexyl, ethylhexyl and hydroxypolyethylene glycol methacrylates;

C6-12 N-alkyl(meth)acrylamides, such as N-octylacrylamide;

vinyl esters with the formula: $R_3$—CO—O—CH=$CH_2$, wherein $R_3$ is chosen from linear and branched alkyl groups comprising from 6 to 12 carbons, such as vinyl neononanoate and vinyl neododecanoate.

Among the monomeric units, said at least one monomeric units resulting from at least one monomer, which is capable of forming a homopolymer with a Tg greater than or equal to 20° C., and some of which may be hydrophilic, as disclosed herein, non-limiting mention may be made of:

vinyl compounds with the formula: $CH_2$=CH—$R_4$, wherein $R_4$ is a group chosen from hydroxyl group; —NH—C(O)—$CH_3$ group, —OC(O)—$CH_3$ group, $C_3$-$C_8$ cycloalkyl groups; $C_6$-$C_{20}$ aryl groups; $C_7$-$C_{30}$ aralkyl groups ($C_1$-$C_4$ alkyl group); heterocyclic groups comprising from 4 to 12 chain members comprising at least one heteroatom chosen from O, N and S; heterocyclylalkyl groups ($C_1$-$C_4$ alkyl), such as furfuryl groups; wherein the cycloalkyl, aryl, aralkyl, heterocyclic, and heterocyclylalkyl groups may optionally be substituted by at least one substituent chosen from hydroxyl group, halogen atoms, and alkyl groups comprising from 1 to 4 carbon atoms, linear and branched, optionally comprising at least one heteroatoms chosen from O, N, S and P, wherein the alkyl groups also may optionally be substituted by at least one substituent chosen from hydroxyl groups, the halogen atoms (such as Cl, Br, I and F), and Si, non-limiting examples of vinyl monomers can be chosen from vinylcyclohexanes, styrenes and vinyl acetates;

acrylates with the formula $CH_2$=CH—$COOR_5$, wherein $R_5$ may be chosen from tert-butyl group, $C_3$-$C_8$ cycloalkyl groups; $C_6$-$C_{20}$ aryl groups; $C_7$-$C_{30}$ aralkyl groups ($C_1$-$C_4$ alkyl group); heterocyclic group comprising from 4 to 12 chain members comprising at least one heteroatom chosen from O, N, and S; heterocyclylalkyl groups ($C_1$-$C_4$ alkyl), such as furfuryl groups; wherein the cycloalkyl, aryl, aralkyl, heterocyclic and heterocyclylalkyl groups may optionally be substituted by at least one substituent chosen from hydroxyl group, halogen atoms, and $C_1$-$C_4$ linear and branched alkyl groups optionally comprising at least one heteroatom chosen from O, N, S and P, wherein the alkyl groups may optionally be substituted by at least one substituent chosen from hydroxyl groups, halogen atoms (such as Cl, Br, I and F), and Si. Non-limiting examples of acrylate monomers may be chosen from t-butylcyclohexyls, tert-butyl, t-butylbenzyl, furfuryl and isobornyl acrylates;

methacrylates with the formula $CH_2$=$C(CH_3)$—$COOR_6$, wherein $R_6$ may be chosen from linear and branched alkyl groups comprising from 1 to 4 carbon atoms, such as a methyl, ethyl, propyl and isobutyl groups, wherein the alkyl groups may optionally be substituted by at least one substituent chosen from hydroxyl group, halogen atoms (such as Cl, Br, I and F), and Si; $C_3$-$C_8$ cycloalkyl groups; $C_6$-$C_{20}$ aryl groups; $C_7$-$C_{30}$ aralkyl groups ($C_1$-$C_4$ alkyl group); heterocyclic groups comprising from 4 to 12 chain members comprising at least one heteroatom chosen from O, N, and S; heterocyclylalkyl groups ($C_1$-$C_4$ alkyl), such as furfuryl groups; wherein the cycloalkyl, aryl, aralkyl, and heterocyclic and heterocyclylalkyl groups may optionally be substituted by at least one substituent chosen from hydroxyl group, halogen atoms, and alkyl groups comprising from 1 to 4 carbon atoms, linear and branched, optionally comprising at least one heteroatom chosen from O, N, S, and P, wherein the alkyl groups may optionally be substituted by at least one substituent chosen from hydroxyl groups and the halogen atoms (such as Cl, Br, I and F), non-limiting examples of methacrylate monomers may be chosen from methyl, ethyl, n-butyl, isobutyl, t-butylcyclohexyl, t-butylbenzyl, methoxyethyl, methoxypropyl and isobornyl methacrylates;

(meth)acrylamides with the formula: $CH_2$=C(R')—CO—$NR_7R_8$, wherein $R_7$ and $R_8$, which may be identical or different, can be chosen form hydrogen and linear and branched alkyl groups comprising from 1 to 12 carbon atoms, such as n-butyl, t-butyl, isopropyl, isohexyl, isooctyl, and isononyl groups, and R' is chosen from H and methyl.

non-limiting examples of (meth)acrylamide monomers may be chosen from N-butylacrylamide, N-t-butylacrylamide, N-isopropylacrylamide, N,N-dimethylacrylamide and N,N-dibutylacrylamide.

For instance, monomers with Tg greater than or equal to 20° C. may be chosen from:

furfuryl, isobornyl, tert-butyl, tert-butylcyclohexyl and tert-butylbenzyl acrylates;

methyl, n-butyl, ethyl and isobutyl methacrylates, styrene, styrene sulphonate;

vinyl acetate and vinylcyclohexane.

A person or ordinary skill in the art should be able to select the monomers and their amounts in relation to the desired result, on the basis of his or her general knowledge, and, for instance, the relative reactivity of each monomer.

Thus, if the desired copolymer is one that has hydrophilic units at the center of a polymer chain, preference should be given to a bifunctional initiator and a mixture of monomers such that the reactivity of the hydrophilic monomers is greater than that of the other monomers.

Furthermore, the methods of preparation employed can make it possible to adjust and control the Tg value or values of the copolymer, and thus obtain a gradient copolymer having at least one Tg value, as disclosed herein.

The gradient copolymers, as disclosed herein, can be prepared by a person or ordinary skill in the art by employing the following procedure:

1) Prepare a mixture of the various monomers, in a solvent if necessary, such as in a stirred reactor. Add a radical polymerization initiator and a polymerization-control agent. One may want to keep the mixture under an atmosphere of gas that is inert with respect to radical polymerization, such as nitrogen or argon.

If a polymerization solvent is required, one may choose from alkyl acetates, such as butyl acetate and ethyl acetate, aromatic solvents, such as toluene, ketone solvents, such as methyl ethyl ketone, and alcohols, such as ethanol. In the case when the mixture of monomers is miscible with water, the latter can be used, for example, as solvent or co-solvent.

2) While stirring, bring the mixture up to the desired polymerization temperature. The temperature most frequently, can range from 10° C. to 160° C., such as from 25° C. to 130° C.

The choice of polymerization temperature is optimized, for example, in relation to the chemical composition of the monomer mixture. Thus, monomers that have very high constants of propagation kinetics and a lower affinity for the control agent may be polymerized, for instance, at low temperatures (for example, in the case of a high proportion of methacrylic derivatives, polymerization will probably occur at a temperature ranging from 25° C. to 80° C.).

3) If necessary, one can modify the polymerization medium during polymerization, before reaching 90% conversion of the initial monomers, by supplementary addition of at least one monomer, such as of the initial mixture. Such an addition can be done in various ways, ranging from a single abrupt addition to continuous addition throughout the polymerization.

4) Stop the polymerization once the desired degree of conversion is reached. The overall composition of the copolymer depends on the degree of conversion. One may wish to stop polymerization after reaching at least 50% conversion, or, such as at least 60% conversion, or after reaching, for example, at least 90% conversion.

5) Any residual monomers can be removed by any known method, such as by evaporation, or by adding an amount of conventional polymerization initiator, such as peroxide or azo derivatives.

As disclosed herein, the polymerization-control agent that can be used is a nitroxide of formula (I), alone or in a mixture:

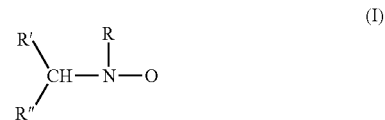

wherein:

R and R', which may be identical or different, may be chosen from linear and branched saturated hydrocarbon (alkyl) groups, comprising from 1 to 40 carbon atoms, optionally substituted by at least one group chosen from —$OR_3$, —$COOR_3$ and —$NHR_3$ (wherein $R_3$ may be chosen from H and linear and branched, saturated hydrocarbon (alkyl) groups, comprising from 1 to 40 carbon atoms), R and R' may additionally be joined so as to form a ring.

For example, R and R', which may be identical or different, can be chosen from linear and branched alkyl groups comprising from 1 to 12 carbon atoms, such as methyl, ethyl, propyl, n-butyl, isobutyl, tert-butyl and pentyl groups. For example, R and R' may both be tert-butyl group;

R" is chosen from monovalent groups of molecular weight (Mw) greater than 16 g/mol, for instance, phosphorus-comprising groups of the formula:

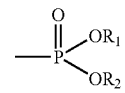

wherein $R_1$ and $R_2$, which may be identical or different, may be chosen from linear and branched, saturated hydrocarbon (alkyl) groups, comprising from 1 to 40 carbon atoms, optionally substituted by at least one group chosen from —$OR_3$, —$COOR_3$ and —$NHR_3$ (wherein $R_3$ may be chosen from hydrogen and a linear and branched, saturated hydrocarbon (alkyl) groups, comprising from 1 to 40 carbon atoms), $R_1$ and $R_2$, additionally, can be joined so as to form a ring.

For example, $R_1$ and $R_2$, which may be identical or different, can be chosen from linear and branched alkyl groups comprising from 1 to 12 carbon atoms, such as methyl, ethyl, propyl, n-butyl, isobutyl, tert-butyl and pentyl groups. For example, $R_1$ and $R_2$ can both be ethyl group.

The radical polymerization initiator can be chosen from all the usual polymerization initiators, such as compounds of the azo type, for example, azobisisobutyronitrile, and of the peroxide type, such as organic peroxides comprising from 6 to 30 carbon atoms, such as benzoyl peroxide.

For example, a nitroxide to initiator molar ratio ranging from 1 to 2.5 can be observed; this ratio can also range from 2 to 2.5 when it is considered that one mole of initiator gives rise to two moles of polymer chains, and can range from 1 to 1.25 for monofunctional initiators.

Certain alkoxyamines can be used as radical polymerization initiators, and can be used, for instance, for initiating polymerization and at the same time releasing the nitroxide controlling the polymerization. As disclosed herein, alkoxyamines can be chosen from those of formula (II):

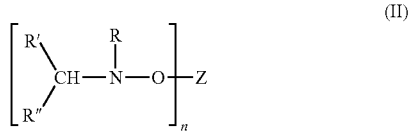

(II)

wherein:
R, R' and R" are as defined above for the nitroxide of formula (I),
n is an integer less than or equal to 8, such as from 1 to 3;
Z is a monovalent or polyvalent radical, such as a styryl, acryl or methacryl radicals.

It is also possible to add a nitroxide of formula (I) to the alkoxyamine of formula (II), in an amount ranging from 0 to 20 mol% relative to the moles of alkoxyamine functions (one mole of polyvalent alkoxyamine supplies a number of alkoxyamine functions proportional to its valency), so as to improve the quality of polymerization control.

A person of ordinary skill in the art should be able to select the initiator in relation to the requirements of the application. Thus, a monofunctional initiator should lead to asymmetric chains, whereas a polyfunctional initiator should lead to macromolecules having a symmetry about a center.

The at least one gradient copolymers, as disclosed herein, can be present in the topical cosmetic or dermatological compositions in an amount ranging from 0.1% to 60% by weight, relative to the total weight of the composition, such as ranging from 0.5% to 40% by weight, relative to the total weight of the composition, for instance, ranging from 1% to 35% by weight, relative to the total weigh of the composition, or such as in an amount ranging from 5% to 30% by weight, relative to the total weight of the composition.

The at least one gradient copolymers can be present in the composition in dissolved form, for example, in water or an organic solvent, or alternatively, in the form of an aqueous or organic dispersion.

It is possible to prepare an aqueous solution of the at least one gradient copolymer directly by mixing the polymer with water and heating it if necessary.

It is also possible to dissolve the at least one copolymer in an organic solvent with a boiling point below that of water (for example, acetone or methyl ethyl ketone) and at a solids content ranging from 20% to 90% by weight, relative to the total weight of the composition.

When the hydrophilic monomers are chosen from acids, then, if desired, a solution of at least 1 M of base, such as salts of hydroxonium ions ($OH^-$), amines (ammonia), carbonates ($CO_3^{2-}$) and hydrogen carbonates ($HCO_3^-$) or of organic neutralizing agents, can be added to the organic solution. When the hydrophilic monomers are chosen from amines, it is possible to add a solution, for example, at least 1M, of acid. While stirring vigorously, water can be added to the solution, wherein the solids content obtained ranges from 1% to 80% by weight, relative to the total weight of the composition. If necessary, the water can be replaced with a water/alcohol mixture, in proportions ranging from 99/1 to 50/50. The solvent is evaporated while stirring the solution at 100° C. Thus, concentration is continued until the desired solids content is obtained.

It has been found that the at least one gradient copolymers, as disclosed herein, can be, for instance, soluble or dispersible in water and/or in organic solvents, such as $C_1$-$C_6$ mono-alcohols, such as ethanol or isopropanol, or esters of carboxylic acids comprising from 3 to 10 carbon atoms, such as butyl acetate; and the at least one gradient copolymer can be dissolved in large quantities without affecting the viscosity of the solution.

For example, compared with the usual diblock copolymers, the gradient copolymers, as disclosed herein, can lead to a lower viscosity; therefore, these gradient copolymers can be introduced into a formulation without greatly altering its viscosity.

For instance, the at least one gradient copolymers display a low viscosity even at concentrations that can range up to 20% by weight of the gradient copolymer in water.

Thus, it has been found that an aqueous solution at 20% by weight of the gradient copolymers could exhibit, for instance, a viscosity ranging from 1 to 10,000 centipoises ("cP"), such as ranging from 1 to 5,000 cP, and, for example, ranging from 5 to 1,000 cP, at 25° C. (the viscosity is measured with a Brookfield viscosimeter, spindle module, the module being chosen as a function of solution viscosity).

In addition to the at least one gradient copolymer, the cosmetic or dermatologic compositions, as disclosed herein, can comprise a medium that is physiologically acceptable, such as cosmetically or dermatologically acceptable, i.e. a medium that is compatible with keratinous substances, such as the skin of the face or body, the hair, eyelashes, eyebrows and the nails.

The composition can thus comprise a hydrophilic medium comprising water or a mixture of water and hydrophilic organic solvent(s), such as alcohols, chosen from linear and branched lower mono-alcohols comprising from 2 to 5 carbon atoms, such as ethanol, isopropanol and n-propanol; polyols such as glycerol, diglycerol, propyleneglycol, sorbitol, pentyleneglycol; polyethylene glycols; $C_2$ ethers; and hydrophilic $C_2$-$C_4$ aldehydes.

The water or the mixture of water and of hydrophilic organic solvents can be present in the composition, as disclosed herein, in an amount ranging from 0.1% to 99% by weight, relative to the total weight of the composition, and such as in an amount ranging from 10% to 80% by weight, relative to the total weight of the composition.

The composition can also comprise fatty phases, for instance, at least one phase comprising of fats that are liquid at room temperature (generally 25° C.) and/or of fats that are solid at room temperature, such as waxes, paste-like fats, gums and their mixtures. The at least one fat can be chosen from animal, vegetable, mineral and synthetic origin. The at least one fatty phase, additionally, can comprise lipophilic organic solvents.

Non-limiting examples of fats that are liquid at room temperature, such as oils, that may be used include: hydrocarbon oils of animal origin, such as perhydrosqualene; vegetable hydrocarbon oils, such as liquid triglycerides of fatty acids comprising from 4 to 10 carbon atoms, such as triglycerides of heptanoic and octanoic acids, sunflower oil, corn oil, soybean oil, grape pip oil, sesame oil, apricot oil, macadamia oil, castor oil, avocado oil, triglycerides of caprylic and capric acids, jojoba oil, shea butter; linear and branched hydrocarbons of mineral and synthetic origin, such as paraffin oils and their derivatives, vaseline™ (petrolatum), polydecenes, hydrogenated polyisobutene, such as parleam; synthetic esters and ethers, for instance, of fatty acids, such as Purcellin oil, isopropyl myristate, ethyl-2-hexyl palmitate, octyl-2-dodecyl stearate, octyl-2-dodecyl erucate, isostearyl isostearate; hydroxylated esters, such as isostearyl lactate, octylhydroxystearate, octyldodecyl hydroxystearate, diisostearylmalate, triisocetyl citrate, heptanoates, octanoates, decanoates of fatty alcohols; polyol esters, such as propyleneglycol dioctanoate, neopentylglycol diheptanoate, diethyleneglycol diisononanoate; and the esters of pentaerythritol; fatty alcohols comprising from 12 to 26 carbon atoms, such as octyldodecanol, 2-butyloctanol, 2-hexyldecanol, 2-undecylpentadecanol, oleic alcohol; fluorinated oils partially hydrocarbonized and/or siliconized; silicone oils, such as volatile and non-volatile polymethylsiloxanes (PDMS), linear and cyclic, liquid and pasty at room temperature, such as cyclomethicones, dimethicones, optionally comprising phenyl groups, such as phenyl trimethicones, phenyltrimethylsiloxydiphenyl siloxanes, diphenylmethyldimethyltrisiloxanes, diphenyl dimethicones, phenyl dimethicones, polymethylphenyl siloxanes; and their mixtures.

The oils can be present, in the composition, in an amount ranging from 0.01% to 90% by weight, relative to the total weight of the composition, such as in an amount ranging from 0.1% to 85% by weight, relative to the total weight of the composition.

The composition, as disclosed herein, can also comprise at least one cosmetically acceptable (such as acceptable tolerance, toxicology and feel) organic solvent.

The at least one solvent can generally be present in an amount ranging from 0% to 90% by weight, relative to the total weight of the composition, such as in an amount ranging from 0.1% to 90% by weight, relative to the total weight of the composition, for instance, ranging from 10% to 90% by weight, relative to the total weight of the composition, and further, for example, in an amount ranging from 30% to 90% by weight, relative to the total weight of the composition.

Not including the hydrophilic organic solvents mentioned above, non-limiting examples of solvents, as disclosed herein, that can be used include, ketones that are liquid at room temperature, such as methyl ethyl ketone, methyl isobutyl ketone, diisobutyl ketone, isophorone, cyclohexanone, and acetone; ethers of propyleneglycol that are liquid at room temperature, such as propyleneglycol monomethyl ether, propyleneglycol monomethyl ether acetate, and dipropyleneglycol mono n-butyl ether; short-chain esters (comprising from 3 to 8 carbon atoms), such as ethyl acetate, methyl acetate, propyl acetate, n-butyl acetate, and isopentyl acetate; ethers that are liquid at room temperature, such as diethyl ether, dimethyl ether and dichlorodiethyl ether; alkanes that are liquid at room temperature, such as decane, heptane, dodecane, isododecane, and cyclohexane; aromatic cyclic compounds that are liquid at room temperature, such as toluene and xylene; aldehydes that are liquid at room temperature, such as benzaldehyde, acetaldehyde and their mixtures.

Wax, according to the present disclosure, means a lipophilic compound, solid at room temperature (25° C.), wherein it has a reversible solid/liquid state and has a melting point greater than or equal to 30° C. which can range to 120° C. By bringing the wax to the liquid state (such as by melting the wax), it is possible to make it miscible with the oils, that may be present in the composition, and form a microscopically homogeneous mixture. But by bringing the temperature of the mixture back to room temperature, one can obtain recrystallization of the wax in the oils of the mixture. The melting point of the wax can be measured by differential scanning calorimetry (DSC), for example, using the calorimeter sold by the company METLER under the designation DSC 30.

The waxes can comprise hydrocarbons, fluorine, and silicones, and can be of vegetable, mineral, animal and synthetic origin. For example, the waxes have a melting point above 25° C., such as above 45° C. Non-limiting examples of the wax, as disclosed herein, include: beeswax, carnauba wax, candelilla wax, paraffin, microcrystalline waxes, ceresine and ozokerite, synthetic waxes, such as polyethylene waxes and Fischer-Tropsch waxes, silicone waxes, such as alkyl and alkoxydimethicone comprising from 16 to 45 carbon atoms.

The gums, can generally comprise polydimethylsiloxanes (PDMS) of high molecular weight, gums of cellulose and of polysaccharides. The pasty substances can generally comprise hydrocarbon compounds, such as lanolins, their derivatives and PDMS.

The type and quantity of the solids, used in the composition, depend on the desired mechanical properties and textures. As a guide, the composition can comprise waxes in an amount ranging from 0% to 50% by weight, relative to the total weight of the composition and, for instance ranging from 1% to 30% by weight, relative to the total weight of the composition.

The composition, as disclosed herein, additionally can comprise at least one colorant chosen from water-soluble colorants, liposoluble colorants, and pulverulent colorants, such as pigments, nacres, and glitters that can be familiar to a person of ordinary skill in the art. The colorants can be present in the composition in an amount ranging from 0.01% to 50% by weight, relative to the weight of the composition, such as in an amount ranging from 0.01% to 30% by weight, relative to the total weight of the composition.

For purposes of the disclosure, pigments designate particles of any form, white and coloured, mineral and organic, insoluble in the physiological medium, used for colouring the composition. Also, for purposes of the disclosure, nacres designate particles of any form, such as the particles produced by certain molluscs in their shell, and the particles that are synthesized.

The pigments can be chosen from white and coloured, mineral and organic. Among the mineral pigments non-liming mention may be made of: titanium dioxide, such as surface-treated titanium dioxide, oxides of zirconium and of cerium, as well as oxides of zinc, of iron (such as black, yellow and red) and of chromium, manganese violet, ultramarine, chromium hydrate and ferric blue, and metal powders, such as aluminium powder and copper powder.

Non-limiting examples of organic pigments that may be mentioned are carbon black, pigments of the D & C type, and lakes based on carmine, barium, strontium, calcium, aluminium.

The nacre pigments can be chosen from white nacre pigments, such as mica coated with titanium and/or with bismuth oxychloride, coloured nacre pigments, such as titanium mica coated with iron oxides, titanium mica coated, for example, with ferric blue or chromium oxide, titanium mica coated with an organic pigment of the type mentioned above, and nacre pigments based on bismuth oxychloride.

Among the water-soluble colorants, non-limiting mention may be made of: disodium salt of ponceau, disodium salt of alizarin green, quinoleine yellow, trisodium salts of amaranth, disodium salt of tartrazine, monosodium salt of rhodamine, disodium salt of fuchsin, xanthophyll, and methylene blue.

The composition, as disclosed herein, can also comprise at least one filler, such as in an amount ranging from 0.01% to 50% by weight, relative to the total weight of the composition, for instance in an amount ranging from 0.01% to 30% by weight, relative to the total weight of the composition. For purposes of the present disclosure, fillers mean particles of any shape, colourless or white, mineral or synthetic, insoluble in the medium of the composition regardless of the temperature at which the composition is manufactured. The fillers, for example, can modify the rheology or the texture of the composition. The fillers can be chosen from mineral, organic, of any shape., plate-like, spherical and oblong, regardless of the crystallographic form (for example, flake, cubic, hexagonal, orthorhombic, etc.). Non-limiting mention can also be made of: talc, mica, silica, kaolin, powders of polyamide (Nylon®) (Orgasol® from Atochem), of poly-β-alanine and of polyethylene, powders of tetrafluoroethylene polymers (Teflon®), lauroyl-lysine, starch, boron nitride, hollow polymer microspheres, such as those of polyvinylidene chloride/acrylonitrile, such as Expancel® (Nobel Industrie), acrylic acid copolymers (Polytrap® from the company Dow Corning) and silicone resin microbeads (Tospearls® from Toshiba, for example), particles of elastomeric polyorganosiloxanes, precipitated calcium carbonates, magnesium carbonates and hydro-carbonates, hydroxyapatite, hollow silica microspheres (Silica Beads® from Maprecos), microcapsules of glass or of ceramic, metal soaps derived from organic carboxylic acids comprising from 8 to 22 carbon atoms, such as from 12 to 18 carbon atoms, for example, zinc stearate, magnesium stearate, lithium stearate, zinc laurate, and magnesium myristate.

The composition can also comprise at least one additional polymer, such as a film-forming polymer. For purposes of the present disclosure, "film-forming polymer" means a polymer that is able to form, on its own or in the presence of an auxiliary film-forming agent, a continuous film that adheres to a substrate, such as to keratinous substances. Among the film-forming polymers that can be used in the composition of the present disclosure, non-limiting mention may be made of synthetic polymers, of the radical type or of the polycondensed type, polymers of natural origin and their mixtures, such as acrylic polymers, polyurethanes, polyesters, polyamides, polyureas, and cellulosic polymers, such as nitrocellulose.

The composition, as disclosed herein, can also comprise at least one ingredient that can be commonly used in cosmetics, such as vitamins, thickening agents, gelling agents, trace elements, softeners, sequestering agents, perfumes, alkalizing or acidifying agents, preservatives, sun filters, surfactants, antioxidants, agents preventing hair loss, anti-filming agents, propellants, ceramides, and their mixtures. A person of ordinary skilled in the art would select any of the supplementary compounds, and/or their quantity, in such a way that the desired properties of the composition, as disclosed herein, are not, or substantially not, impaired by the addition envisaged.

The composition, according to the present disclosure, can be in a form chosen from suspensions, dispersions, solutions, gels, emulsions, such as oil-in-water (O/W) and water-in-oil (W/O) emulsions, and multiple emulsions (W/O/W or polyol/ O/W or O/W/O), creams, pastes, foams, dispersions of vesicles, such as ionic and non-ionic lipids, biphase and multiphase lotions, sprays, powders, pastes, such as flexible paste (for instance, paste comprising a dynamic viscosity at 25° C. of the order of 0.1 to 40 Pa.s at a shear rate of 200 s$^{-1}$, after 10 minutes of measurement in cone/plate geometry). The composition can also be anhydrous, for example, it can be an anhydrous paste.

A person of ordinary skill in the art should be able to choose the at least one galenic form, as well as its method of preparation, on the basis of his or her general knowledge, taking into account on the one hand the nature of the constituents used, such as their solubility in the carrier, and on the other hand the application envisaged for the composition.

The composition, as disclosed herein, can be a make-up composition, such as a product for the complexion, such as foundation, blusher and eyeshadow; a product for the lips, such as lipstick and lip-care product; an anti-ring product; blusher; mascara; eyeliner; a make-up product for the eyebrows, lip and eye pencil; a product for the nails, such as nail varnish and nail-care product; a make-up product for the body; a make-up product for the hair (for instance, hair mascara and lacquer).

The composition, according to the present disclosure, can be in a form chosen from compositions for protection or care of the skin of the face, of the neck, of the hands and of the body, such as anti-wrinkle and anti-fatigue compositions that can give the skin a fresh appearance; moisturizing and treatment compositions; sun-protection and artificial tanning compositions.

The composition, as disclosed herein, can also be in a form chosen from haircare products, such as for hairdressing and for maintaining a hairstyle. The haircare compositions, for example, are chosen from shampoos, gels, setting lotions, blow-drying lotions, fixing and hairdressing compositions, such as lacquers and sprays. The lotions can be packaged in various forms chosen from atomizers, spray bottles and in aerosol containers to provide application of the composition as a spray and as a mousse. Such forms of packaging are indicated, for example, when we wish to obtain a spray or mousse for fixing or treating the hair.

The disclosure also relates to a cosmetic method for make-up or care of keratinous substances, such as the skin of the body and of the face, the nails, the hair and/or the eyelashes, comprising applying cosmetic compositions as defined previously on the said substances.

The disclosure is illustrated in more detail in the following examples.

For information, Table 1 hereunder gives the coefficients of relative reactivity of the monomers used in the examples:

| M1 | M2 | | | | |
|---|---|---|---|---|---|
| | Acrylate | Styrene | Methacrylate | Methacrylic acid | Acrylic acid |
| Acrylate | 1 | 0.18 | 0.11 | 0.31 | 0.91 |
| Styrene | 0.84 | 1 | 0.478 | 0.418 | 0.25 |
| Methacryl-ate | 2.8 | 0.585 | 1 | 1.28 | / |
| Methacryl-ic acid | 1.25 | 0.6 | 0.48 | 1 | / |
| Acrylic acid | 1.31 | 0.136 | / | / | 1 |

In these examples, the polymerization control agent used was the stable nitroxide, called SG1, with the formula:

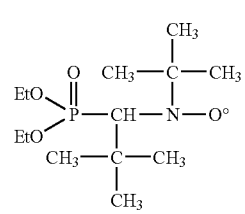

The polymerization initiators mentioned in the examples were alkoxyamines called "DIAMS" and "MONAMS" which correspond to the following formulae:

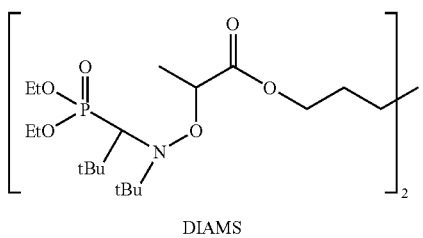

DIAMS

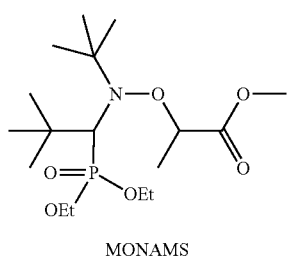

MONAMS

EXAMPLE 1

Bulk Synthesis of Gradient Copolymer

The mixture of reactants was as follows:
MONAMS: 3.0 g
SG1: 0.18 g
Ethyl acrylate: 480 g i.e. 80% by weight relative to the total weight of monomers
Styrene: 60 g i.e. 10% by weight relative to the total weight of monomers
Methacrylic acid: 60 g i.e. 10% by weight relative to the total weight of monomers All the constituents were mixed together, without solvent, under a nitrogen atmosphere, then heated to a temperature that was maintained ranging from 110 to 115° C. for 198 minutes. The reaction was stopped at a degree of conversion of 60%.

Calculation of the gradient by simulation gave the curve shown below. Theoretical prediction gave 30% incorporation of the mixture (styrene/methacrylic acid) and 70% ethyl acrylate.

The validity of this model was provided by monitoring the relative concentrations of the three monomers by gas chromatography and NMR analysis of the polymers.

Figure 3:
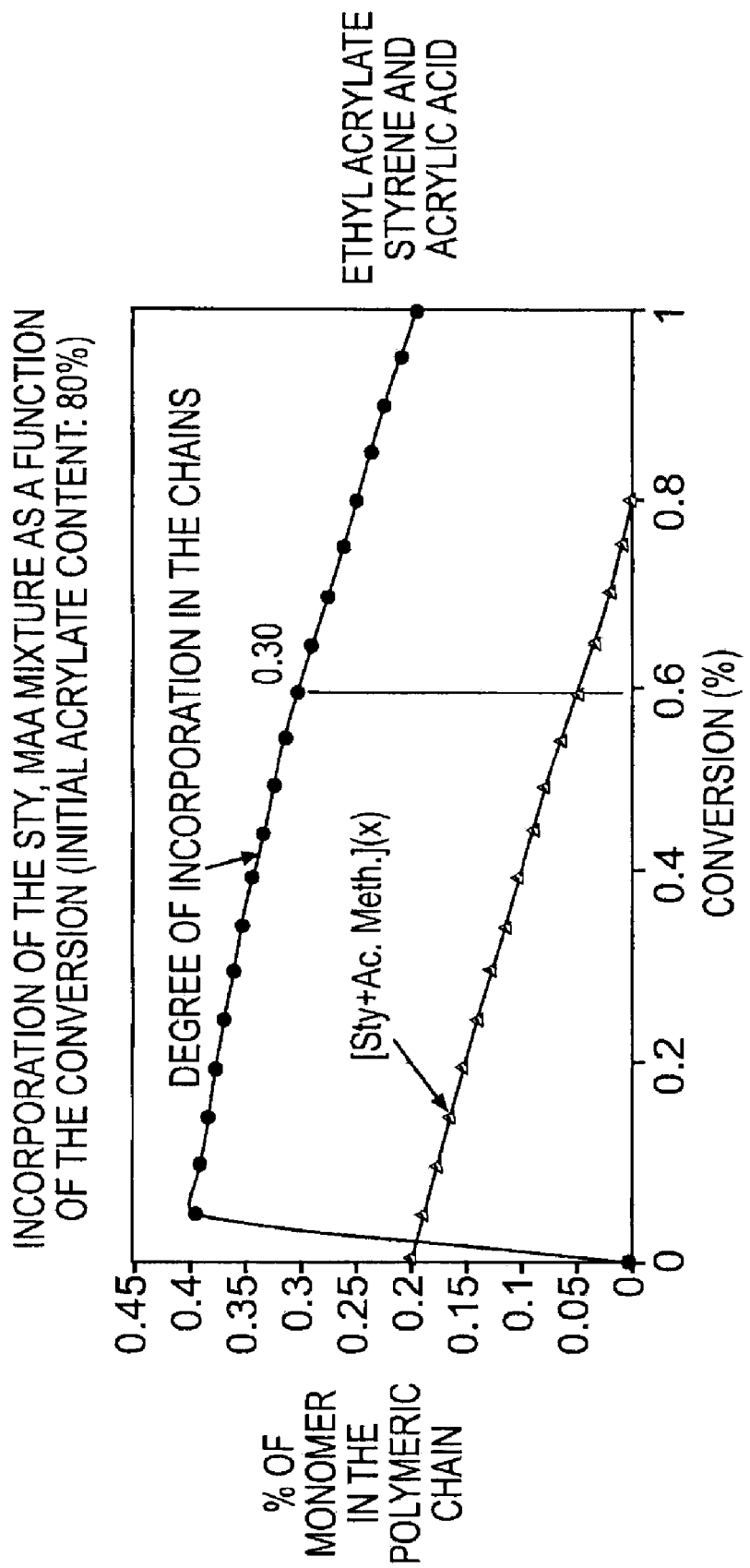
FIG. 3 shows an NMR analysis of the gradient copolymer of Example 1.

Using these methods, it was found that at 60% conversion, the final chemical composition of the copolymer was as follows (wt %): 68.4% ethyl acrylate, 16.1% styrene and 15.5% methacrylic acid according to NMR on the calculated curve (69%) demonstrated in FIG. 3.

Figure 4:
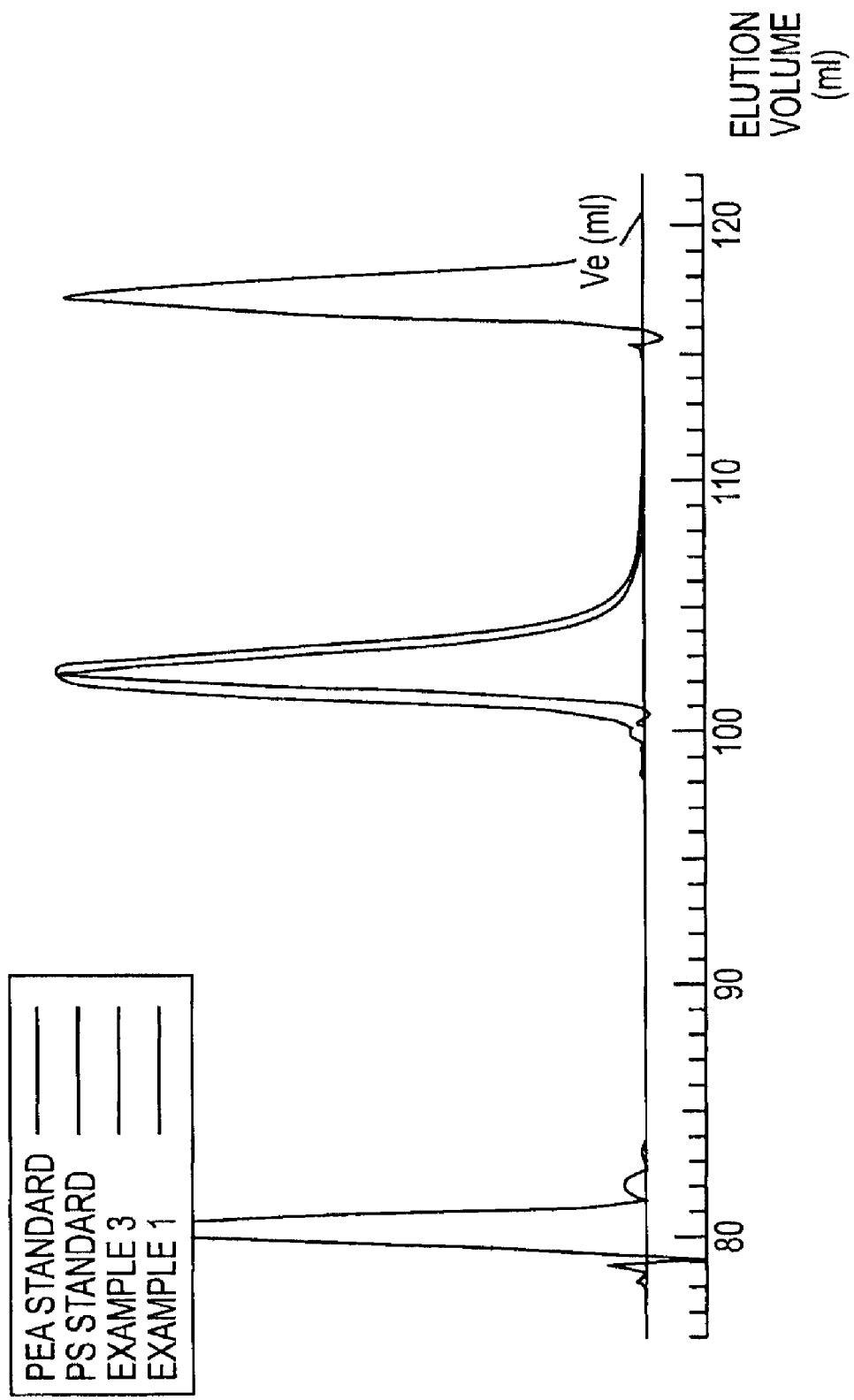
FIG. 4 shows a chromatograph of the gradient copolymer of Example 1 obtained from a liquid adsorption chromatography analysis.

Using LAC, the trace of the polymer showed the low polydispersity of the chemical composition of the chains, as demonstrated in FIG. 4.

Measurement of the molecular weights by steric exclusion chromatography lead to the following results:

Mn was equal to 32,140 g/mol and Mw was equal to 51,700 g/mol, hence the polydispersity index Ip was equal to 1.6.

The composition dispersity (or w) was 1.6.

Figure 5:
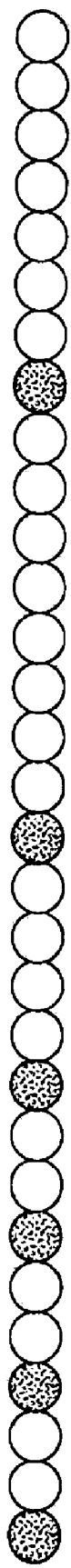
FIG. 5 shows a schematic representation of the gradient copolymer of Example 1.

FIG. 5 demonstrates a possible schematic representation of the copolymer that was obtained, wherein the darkened units denote the styrene/methacrylic acid linkages, and the white units denote the ethyl acrylate linkages.

EXAMPLE 2

Bulk Synthesis of Gradient Copolymer

Following the procedure described in example 1, various copolymers were prepared from the following mixture of reactants:
MONAMS: 3.0 g
SG1: 0.18 g
Styrene: 60 g
Methacrylic acid: 60 g
Acrylate (or acrylate mixture): 480 g

| Example | Acrylate | Characteristics of the copolymer | Final composition of the copolymer (wt %) |
|---|---|---|---|
| 2a | Butyl acrylate | Mn = 31,100 g/mol<br>Mw = 52,930 g/mol<br>Ip = 1.7 | Styrene: 18<br>Methacrylic acid: 22<br>Butyl acrylate: 60 |
| 2b | Methyl acrylate | Mn = 32,750 g/mol<br>Mw = 61,470 g/mol<br>Ip = 1.88 | Styrene: 20<br>Methacrylic acid: 21<br>Methyl acrylate: 59 |
| 2c | Mixture 50/50 by weight butyl acrylate/ethyl acrylate | Mn = 29,690 g/mol<br>Mw = 51,630 g/mol<br>Ip = 1.74 | Styrene: 18<br>Methacrylic acid: 16<br>Acrylates: 66 |

EXAMPLE 3

Synthesis in the Presence of Solvent

The same synthesis as in example 1 was carried out, but with solvent present. The mixture of reactants was as follows:
MONAMS: 3.43 g
SG1: 0.2 g
Ethyl acrylate: 336 g
Styrene: 42 g
Methacrylic acid: 42 g
Toluene: 180 g All of the constituents were mixed together, in the toluene as solvent, under a nitrogen atmosphere, then heated to a temperature that was maintained ranging from 110 to 115° C., for 198 minutes.

The final degree of conversion was 82%, and the solids content obtained was 57.2% by weight.

The following analytical results were found: Mn was equal to 30,570 g/mol, Mw was equal to 50,500 g/mol and Ip was equal to 1.65.

The composition dispersity (or w) was 2.0.

The final composition of the copolymer was found by liquid adsorption chromatography (LAC), which showed similarity of composition with the copolymer prepared in example 1 and absence of homopolymer in the materials. This was illustrated by FIG. 4 given in example 1.

EXAMPLE 4

Synthesis in the Presence of Solvent

Following the procedure in example 3, at 120° C. and for 400 minutes, a new copolymer was synthesized, but in a different solvent: methyl ethyl ketone.

The initial composition of the mixture was:
MONAMS: 4.893 g
SG1: 0.2881 g
Ethyl acrylate: 293.8 g
Methyl acrylate: 32.66 g
Styrene: 76.8 g
Methacrylic acid: 76.8 g
Methyl ethyl ketone: 120 g The final degree of conversion was 99%, and the solids content obtained was 79.9%.

The following analytical results were determined:
Mn was equal to 30,500 g/mol
Mw was equal to 58,000 g/mol
Ip was equal to 1.9

The incorporation of the monomers over time was measured by monitoring the proportions of residual monomers (in %) in the course of time (in minutes) by gas chromatography:

| Time | | 0 | 75 | 130 | 190 | 290 | 400 |
|---|---|---|---|---|---|---|---|
| Overall conversion | | 0 | 16 | 30.5 | 49.5 | 85.4 | 99 |
| residual (%) | MeA | 5.45 | 5.1 | 3.75 | 3.75 | 1.6 | 0.13 |
| | EA | 48.95 | | | | 17.95 | 1.2 |
| | MAA | 12.8 | 12.15 | 4.6 | 2 | 0.35 | 0.08 |
| | S | 12.8 | 12.46 | 6.7 | 3.92 | 0.15 | 0.007 |

EA: ethyl acrylate
MeA: methyl acrylate
S: styrene
MAA: methacrylic acid

*the total residual content was calculated taking into account the solvent, quantified by the solids content.

Figure 6:
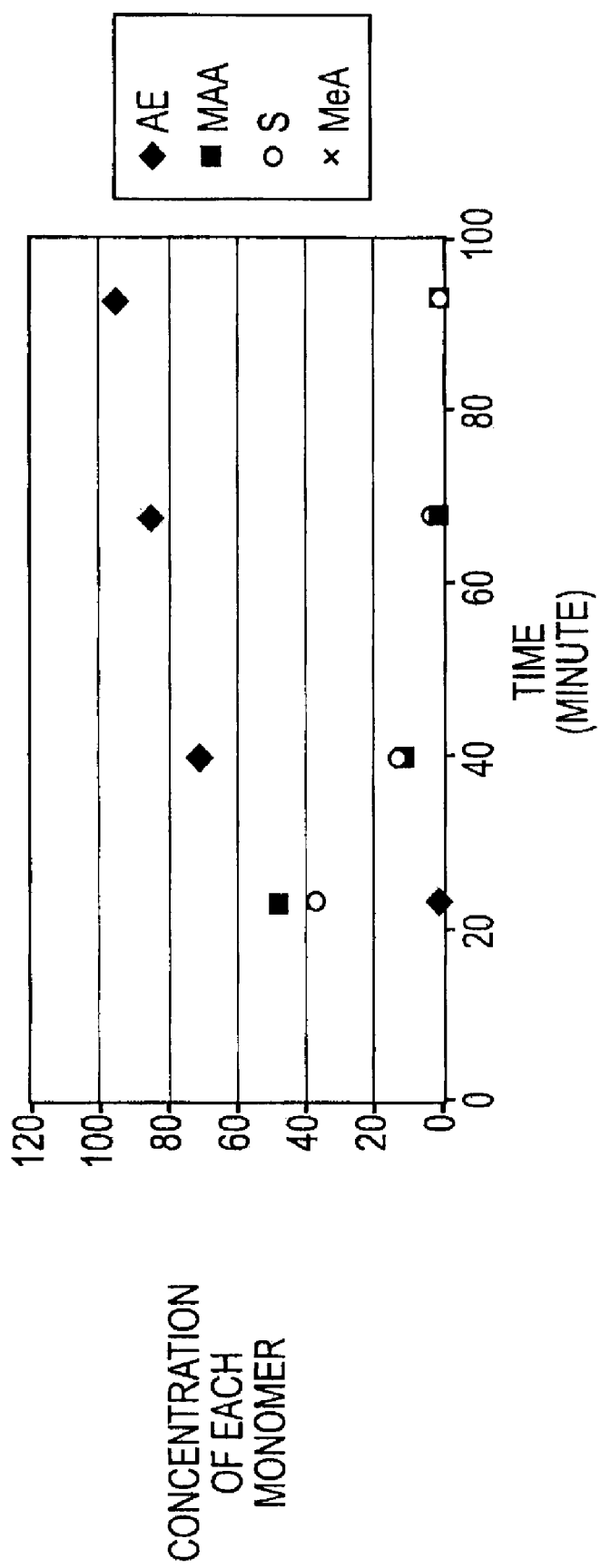
FIG. 6 shows calculated gradients determined for each monomer of the gradient copolymer of Example 4.

It was noted that each monomer was present throughout the reaction. The gradient determined for each monomer could then be calculated, and gave the curves demonstrated in FIG. 6.

The final composition of the copolymer was as follows:
ethyl acrylate: 34% by weight
methyl acrylate: 34% by weight
styrene: 16% by weight
methacrylic acid: 16% by weight

EXAMPLE 5

Prepared an aqueous dispersion at 10% solids content of the copolymer prepared in example 2a.

To do this, the polymer was first dried in the stove. Then 10 g of polymer, which comprised 1.6 g of AMP(amino-2-methyl-2-propanol), was dissolved in 90 ml of water. A clear, very thin aqueous dispersion was obtained. The particle size, measured by light scattering (Coulter 4NW apparatus) was 33 nm.

EXAMPLE 6

Prepared an aqueous dispersion of the copolymer prepared in example 1.

Dissolved 10 g of polymer in 40 g of tetrahydrofuran; added 1.41 g of AMP (amino-2-methyl-2-propanol) dissolved in 10 ml of water. The solution became thicker. Then while stirring vigorously slowly added, 90 ml of demineralized water. The solution remained clear, and became fluid again.

The solvent was evaporated and a clear, thin aqueous dispersion was obtained. The particle size measured by light scattering (Coulter 4NW apparatus) was 199 nm.

EXAMPLE 7

Dissolved the polymers of examples 1 and 2a in butyl acetate and so obtained a solution having a dry matter content of 20% by weight (viscosity at 25° C.: less than 500 cP).

A composition was obtained that could be applied to the nails. It was also possible for it to be pigmented.

EXAMPLE 8

Prepared aqueous dispersions at 4.6% by weight of dry matter from the dispersions in examples 5 and 6.

Then prepared an aerosol spray comprised of:
65 g of aqueous dispersion of polymer at 4.6% by weight, of dry matter
35 g of DME (dimethylether)

EXAMPLE 9

The rheological properties of an aqueous gel at 22.3% by weight of gradient copolymer of poly(butyl acrylate)/(styrene/neutralized methacrylic acid), as disclosed herein, were investigated in comparison with those of aqueous gels at various concentrations, of poly(butyl acrylate)/(styrene/neutralized methacrylic acid) diblock copolymer.

| Polymer | Monomers | wt. % | Molecular weights |
|---|---|---|---|
| Gradient polymer as disclosed herein (dry extract 22.3%) | Butyl acrylate | 59.6 | Mn = 31,110 |
| | Styrene | 17.5 | Mw = 52,930 |
| | Neutralized methacrylic acid | 22.9 | |

The measurements were carried out at 25° C. using a Haake RS150 controlled-stress rheometer, equipped with a sand-blasted-titanium measuring system fitted with an anti-evaporation device. A cone and plate measuring system was used with diameter of 6 cm and angle of 2°. The specimen was put in place gently (elevator speed 0.6 mm/min) and it was left to rest for 2 minutes before beginning the measurements.

Viscoelastic Behaviour (Measurements with Vibrations)

It was found that the copolymer, disclosed herein, was characterized by low consistency, notably at low frequency, which increased with the stress. Moreover, it possessed a pronounced liquid character that remained practically the same over the entire frequency range investigated (0.01, 1 and 10 Hz).

Comparison of the linear viscoelastic properties obtained at a frequency of 1 Hz for the gradient copolymer and the diblock copolymer showed differences in properties and in behaviour between the two copolymers. The 22.3% gradient copolymer had a fairly low consistency that was between those of the diblock copolymer gels, at concentrations of 2.4 and 1.04%. The gradient copolymer differed from the diblock copolymer by its pronounced liquid character which was not obtained even for the lowest concentrations of diblock copolymer.

Behaviour Under Shear (with Controlled Speed and Controlled Stress)

Comparison of the flow profile obtained for the gradient copolymer and those obtained for the different concentrations (1.04%, 2.4%, 4.5%, 7.13% and 11.4% by weight of dry matter) of diblock copolymer showed large differences in behaviour between the two copolymers.

The gradient copolymer (at 22.3% of dry extract) possessed a wide pseudo-plateau, where the viscosity at rest was lower than that of the diblock copolymer at 1.04%. In comparison with the diblock copolymer, the gradient copolymer fluidized starting at higher stresses and rates of shear. Fluidization of the gradient copolymer took place very slowly, and its viscosity at rest decreased by a factor of 5 under the action of very strong shear (1000 s$^{-1}$). The viscosities obtained at very high shear rates, for the gradient copolymer at 22.3%, were equivalent to those obtained for the diblock copolymer at 11.4%, whose viscosity at rest was 1000 times higher.

In conclusion, the gradient copolymer, as disclosed herein, was characterized by low consistency and a pronounced liquid character, whereas the chemically equivalent diblock copolymer was characterized by high consistency and a pronounced solid character, even for much lower concentrations (up to 2%).

Moreover, the gradient copolymer had a fairly low viscosity at rest (up to 20 times lower) than that of the diblock copolymer; it fluidized little, and at a slower rate, under the action of shear, as compared with the diblock copolymer.

Figure 7:
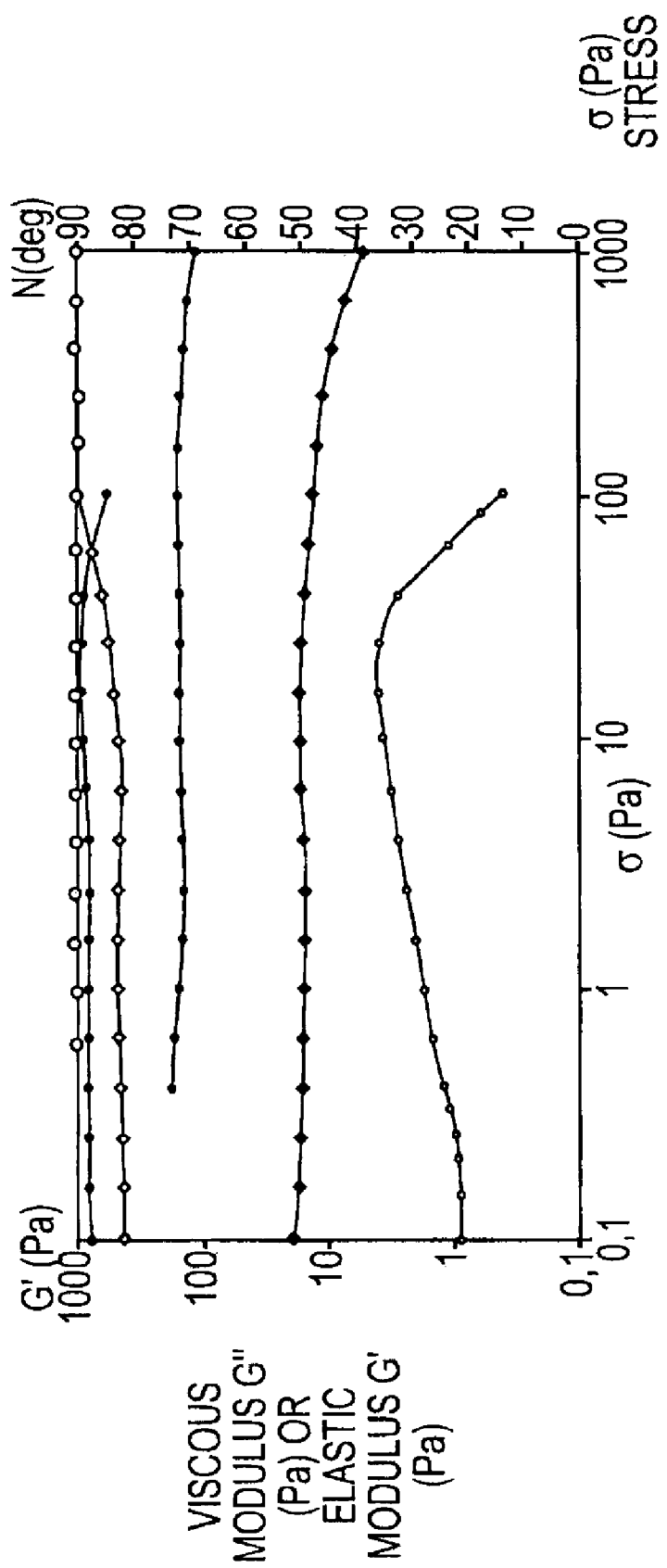
FIG. 7 shows flow profiles of the inventive gradient polymer and comparative diblock copolymer in Example 9.

Thus, a system obtained with a gradient copolymer, even when used at high concentration, was thinner (low viscosity at rest) than that obtained with a chemically equivalent diblock, used at a far lower concentration, as demonstrated in FIG. 7.

What is claimed is:

1. A cosmetic or dermatological composition comprising at least one gradient copolymer comprising at least two different monomeric residues,
   wherein at least one monomeric residue is a hydrophilic monomeric residue, which is present in an amount ranging from 2% to 70% by weight, relative to the total weight of the copolymer, chosen from residues of:
   derivatives of $C_1$-$C_4$ aminoalkyl (meth)acrylates
   $C_1$-$C_4$ N,N-dialkyl(meth)acrylamides and $C_1$-$C_4$ N,N-dialkyl$C_1$-$C_6$aminoalkyl(meth)acrylamides,
   C1-C8 dialkyldiallylamines;
   vinylamines;
   vinylpyridines;
   acid salts thereof and quaternized forms thereof;
   ethylenic carboxylic acids;
   carboxylic anhydrides comprising at least one vinyl bond;
   ethylenic sulphonic acids and their salts;
   vinyl benzoic acids, vinylphosphonic acids and their salts;
   potassium salts of acryloyloxy-3-sulphopropyl, and the compounds of formula $CH_2$=$CHCOOCH_2OCH_2(OH)CH_2SO_3^-Na^+$;
   amides of unsaturated carboxylic acids;
   hydroxyalkyl (meth)acrylates;
   (meth)acrylates of polyethylene glycol (5 to 100 EO) and of glycol, which may be additionally substituted on their terminal function by at least one group chosen from alkyl, phosphate, phosphonate and sulphonate groups;
   alkoxyalkyl (meth)acrylates;
   (meth)acrylates of polysaccharides;
   vinylamides;
   vinyl ethers;
   methacrylamidopropoxytrimethylammoniumbetaines;
   N,N-dimethyl-N-methacryloxyethyl-N-(3-sulphopropyl) ammoniumbetaines,
   3-methacryloylethoxycarbonylpyridiniums;
   a compound of formula:

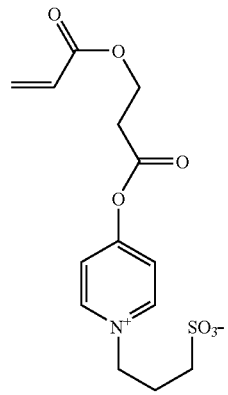

and 4-vinylpyridiniumsulphopropylbetaine of formula:

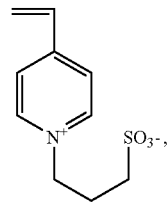

and
wherein at least one other monomeric residue results from at least one monomer which is capable of forming a homopolymer with a Tg less than or equal to 20° C., and which is present in an amount ranging from 10% to 90% by weight, relative to the total weight of the copolymer, the at least one monomer chosen from:

ethylenic hydrocarbons comprising from 2 to 10 carbons;

acrylates with the formula $CH_2$=$CHCOOR_1$, wherein $R_1$ is chosen from saturated and unsaturated hydrocarbon groups, comprising from 1 to 12 carbons, which may be linear and branched with the exception of the tert-butyl group, optionally comprising at least one heteroatom chosen from O, N, S, and Si, wherein the alkyl groups are optionally substituted by at least one substituent chosen from hydroxyl groups and halogen atoms chosen from Cl, Br, I and F;

$R_1$ can also be chosen from groups of formula: —(R")x-(OC$_2$H$_4$)$_n$—OR', wherein x is an integer chosen from 0 and 1, R" is chosen from saturated and unsaturated, linear and branched hydrocarbon groups, comprising from 1 to 12 carbon atoms, n is an integer chosen from 5 to 100 and R' is chosen from H and CH$_3$;

methacrylates with formula: $CH_2$=$C(CH_3)$—COOR$_2$, wherein $R_2$ is chosen from saturated and unsaturated, linear and branched, hydrocarbon groups, comprising from 3 to 12 carbon atoms, optionally comprising at least one heteroatom chosen from O, N, S and Si, wherein the alkyl groups are optionally substituted by at least one substituent chosen from hydroxyl groups and halogen atoms chosen from Cl, Br, I, and F; $R_2$ is also chosen from groups of formula: —(R")x-(OC$_2$H$_4$)$_n$—OR', wherein x is an integer chosen from 0 and 1, R" is chosen from saturated and unsaturated, linear and branched, hydrocarbon groups comprising from 1 to 12 carbon atoms, n is an integer chosen from 5 to 100, and R' is chosen from H and $CH_3$;

N- and N,N-substituted derivatives of amides of $C_{1-12}$ unsaturated carboxylic acids;

vinyl esters of formula: $R_3$—CO—O—CH=$CH_2$ wherein $R_3$ is chosen from linear and branched alkyl groups comprising from 2 to 12 carbon atoms; and vinyl alkyl ethers comprising from 1 to 12 carbon atoms, wherein the at least one gradient copolymer exhibits a mass polydispersity index (Ip) less than or equal to 2.5.

2. The composition according to claim 1, wherein the at least one gradient copolymer exhibits a mass polydispersity index (Ip) ranging from 1.1 to 2.3.

3. The composition according to claim 2, wherein the at least one gradient copolymer exhibits a mass polydispersity index (Ip) ranging from 1.15 to 2.0.

4. The composition according to claim 3, wherein the at least one gradient copolymer exhibits a mass polydispersity index (Ip) ranging from 1.2 to 1.9.

5. The composition according to claim 1, wherein the weight-average molecular weight of the at least one gradient copolymer ranges from 5,000 g/mol to 1,000,000 g/mol.

6. The composition according to claim 5, wherein the weight-average molecular weight of the at least one gradient copolymer ranges from 5,500 g/mol to 800,000 g/mol.

7. The composition according to claim 6, wherein the weight average molecular weight of the at least one gradient copolymer ranges from 6,000 g/mol to 500,000 g/mol.

8. The composition according claim 1, wherein the number-average molecular weight of the at least one gradient copolymer ranges from 5,000 g/mol to 1,000,000 g/mol.

9. The composition according to claim 8, wherein the number-average molecular weight of the at least one gradient copolymer ranges from 5,500 g/mol to 800,000 g/mol.

10. The composition according to claim 9, wherein the number-average molecular weight of the at least one gradient copolymer ranges from 6,000 g/mol to 500,000 g/mol.

11. The composition according to claim 1, wherein the at least one gradient copolymer comprises polymer chains comprising at least one monomeric residue, Mi, wherein there is a non-zero probability of finding the monomeric residue Mi along the polymer chain, regardless of the normalized position x on the polymer chain.

12. The composition according to claim 1, wherein the at least one gradient copolymer is such that on a curve of liquid adsorption chromatography ("LAC"), which shows the proportion of polymers as a function of the elution volume, the difference ($V^{1/2}max-V^{1/2}min$) is less than or equal to 3.5, wherein "$V^{1/2}min$" is the minimum value of the elution volume at mid-height of the curve, and "$V^{1/2}max$" is the maximum value of the elution volume at mid-height of the curve.

13. The composition according to claim 12, wherein the difference ($V^{1/2}max-V^{1/2}min$) ranges from 1 to 2.8.

14. The composition according to claim 13, wherein the difference ($V^{1/2}max-V^{1/2}min$) ranges from 1.2 to 2.5.

15. The composition according to claim 1, wherein the at least one hydrophilic monomeric residue is present in an amount ranging from 5% to 50% by weight, relative to the total weight of the copolymer.

16. The composition according to claim 15, wherein the at least one hydrophilic monomeric residue is present in an amount ranging from 10% to 30% by weight, relative to the total weight of the copolymer.

17. The composition, according to claim 1, wherein the homopolymer has a Tg ranging from −150° C. to 20° C.

18. The composition, according to claim 17, wherein the homopolymer has a Tg ranging from −130° C. to 18° C.

19. The composition, according to claim 18, wherein the homopolymer has a Tg ranging from −120° C. to 15° C.

20. The composition according to claim 1, wherein the at least one monomeric residue which is capable of forming a homopolymer with a Tg less than or equal to 20° C. is present in an amount ranging from 20% to 80% by weight, relative to the total weight of the copolymer.

21. The composition according to claim 20, wherein the at least one monomeric residue is present in an amount ranging from 50% to 75% by weight, relative to the total weight of the copolymer.

22. The composition according to claim 1, wherein the derivates of $C_1$-$C_6$ aminoalkyl (meth)acrylates are chosen from N,N-di($C_1$-$C_4$)alkylamino($C_1$-$C_6$)alkyl (meth)acrylates.

23. The composition according to claim 22, wherein the N,N-di($C_1$-$C_4$)alkylamino($C_1$-$C_6$)alkyl (meth)acrylates are chosen from N,N-dimethylaminoethyl methacrylate (MADAME) and N,N-diethylaminoethyl methacrylate (DEAMEA).

24. The composition according to claim 1, wherein the $C_1$-$C_4$ N,N-dialkyl(meth)acrylamides and $C_1$-$C_4$N,N-dialkyl$C_1$-$C_6$aminoalkyl(meth)acrylamides are chosen from N,N-dimethylacrylamide, N,N-dimethylaminopropylacrylamide (DMAPA), and N,N-dimethylaminopropylmethacrylamide (DMAPMA).

25. The composition according to claim 1, wherein the $C_1$-$C_8$ dialkyldiallylamines are chosen from dimethyldiallylamine.

26. The composition according to claim 1, wherein the vinylpyridines are chosen from 2-vinylpyridine and 4-vinylpyridine.

27. The composition according to claim 1, wherein the ethylenic carboxylic acids are chosen from acrylic, methacrylic, crotonic, itaconic, fumaric, and maleic acids.

28. The composition according to claim 27, wherein the ethylenic carboxylic acids are chosen from acrylic acid.

29. The composition according to claim 1, wherein the carboxylic anhydrides comprising at least one vinyl bond are chosen from maleic anhydride.

30. The composition according to claim 1, wherein the ethylenic sulphonic acids are chosen from styrenesulphonic acid and acrylamidopropanesulphonic acid.

31. The composition according to claim 1, wherein the amides of unsaturated carboxylic acids are chosen from acrylamide, methacrylamide, and their N-substituted derivatives.

32. The composition according to claim 31, wherein the N-substituted derivatives are chosen from $C_1$-$C_4$ N-alkyl (meth)acrylamides and $C_1$-$C_4$ N,N-dialkyl(meth)acrylamides.

33. The composition according to claim 32, wherein the $C_1$-$C_4$ N-alkyl(meth)acrylamides are chosen from N-methylacrylamide.

34. The composition according to claim 32, wherein the $C_1$-$C_4$ N,N-dialkyl(meth)acrylamides are chosen from N,N-dimethylacrylamide.

35. The composition according to claim 1, wherein the hydroxyalkyl (meth)acrylates are chosen from those wherein the alkyl group comprises from 2 to 4 carbon atoms.

36. The composition according to claim 35, wherein the hydroxyalkyl (meth)acrylates are chosen from hydroxyethyl (meth)acrylate.

37. The composition according to claim 1, wherein the (meth)acrylates of polyethylene glycol (5 to 100 EO) and of glycol, which may be additionally substituted on their terminal function by at least one group chosen from alkyl, phosphate, phosphonate and sulphonate groups, are chosen from glycerol acrylates, methoxypolyethylene glycols (meth)acrylates (8 and 12 EO), and hydroxypolyethylene glycol (meth) acrylates.

38. The composition according to claim 1, wherein the alkoxyalkyl (meth)acrylates are chosen from ethoxyethyl (meth)acrylates.

39. The composition according the claim 1, wherein the (meth)acrylates of polysaccharides are chosen from sucrose acrylate.

40. The composition according the claim 1, wherein the vinylamides are chosen from vinyl acetamide and cyclic vinylamides.

41. The composition according to claim 40, wherein the cyclic vinylamides are chosen from vinyl lactams.

42. The composition according to claim 41, wherein the vinyl lactams are chosen from N-vinylpyrrolidones and N-vinylcaprolactams.

43. The composition according the claim 1, wherein the vinyl ethers are chosen from vinyl methyl ether.

44. The composition according to claim 1, wherein the at least one gradient copolymer comprises at least one hydrophilic monomeric residue chosen from residues of N,N-dimethylaminoethyl methacrylate (MADAME), acrylic acid, methacrylic acid, crotonic acid, styrenesulphonic acid, acrylamidopropanesulphonic acid, dimethylaminopropylmethacrylamide (DMAPMA), styrene sulphonate, hydroxyethyl acrylate, glycerol acrylate, ethoxyethyl methacrylate, ethoxyethyl acrylate, methoxypolyethylene glycol (meth) acrylate (8 and 12 EO), hydroxypolyethylene glycol (meth) acrylate, N-vinylpyrrolidone, N-vinylcaprolactam, acrylamides, and N,N-dimethylacrylamide.

45. The composition according to claim 1, wherein the at least one gradient copolymer comprises at least one monomeric residue chosen from residues of $C_1$-$C_4$ alkyl (meth) acrylates, leading to (meth)acrylic acid after hydrolysis.

46. The composition according to claim 45, wherein the $C_1$-$C_4$ alkyl (meth)acrylates are chosen from tert-butyl (meth) acrylates and ethyl (meth)acrylates.

47. The composition according to claim 1, wherein the ethylenic hydrocarbons comprising from 2 to 10 carbons are chosen from ethylenes, isoprenes, and butadienes.

48. The composition according to claim 1, wherein the N- and N,N-substituted derivatives of amides of $C_{1-12}$ unsaturated carboxylic acids are chosen from $C_{1-12}$ N-alkyl(meth) acrylamides.

49. The composition according to claim 48, wherein the $C_{1-12}$ N-alkyl(meth)acrylamides are chosen from N-octylacrylamide.

50. The composition according to claim 1, wherein the vinyl esters are chosen from vinyl propionates, vinyl butyrates, vinyl ethylhexanoates, vinyl neononanoates, and vinyl neododecanoates.

51. The composition according to claim 1, wherein the vinyl alkyl ethers comprising from 1 to 12 carbon atoms are chosen from vinyl methyl ethers, and vinyl ethyl ethers.

52. The composition according to claim 1, wherein the at least one gradient copolymer comprises at least one monomeric residue, said at least one other monomeric residue resulting from at least one monomer which is capable of forming a homopolymer with a Tg less than or equal to 20° C., wherein the at least one monomer is chosen from:
  isoprenes and butadienes;
  methyl, ethyl, isobutyl, n-butyl, ethylhexyl, methoxyethyl, ethoxyethyl and hydroxypolyethylene glycol acrylates;

ethoxyethyl, hexyl, ethylhexyl and hydroxypolyethylene glycol methacrylates;
$C_{6-12}$ N-alkyl(meth)acrylamides;
vinyl esters with the formula: $R_3$—CO—O—CH=$CH_2$ wherein $R_3$ is chosen from linear and branched alkyl groups comprising from 6 to 12 carbon atoms.

53. The composition according to claim 52, wherein the $C_{6-12}$ N-alkyl(meth)acrylamides are chosen from N-octylacrylamide.

54. The composition according to claim 52, wherein the vinyl esters are chosen from vinyl neononanoates and vinyl neododecanoates.

55. The composition according to claim 1, wherein the at least one gradient copolymer further comprises at least one additional monomeric residue, said at least one additional monomeric residue resulting from at least one monomer which is capable of forming a homopolymer with a Tg greater than or equal to 20° C., wherein the at least one monomer is chosen from:
  vinyl compounds with the formula: $CH_2$=CH—$R_4$, wherein $R_4$ is chosen from hydroxyl group; —NH—C(O)—$CH_3$ group, —OC(O)—$CH_3$ group, $C_3$-$C_8$ cycloalkyl groups; $C_6$-$C_{20}$ aryl groups; $C_7$ to $C_{30}$ aralkyl groups ($C_1$-$C_4$ alkyl groups); heterocyclic groups comprising from 4 to 12 chain members comprising at least one heteroatom chosen from O, N and S; heterocyclylalkyl groups ($C_1$-$C_4$ alkyl); wherein the cycloalkyl, aryl, aralkyl, heterocyclic, and heterocyclylalkyl groups are optionally substituted by at least one substituent chosen from hydroxyl group, halogen atoms, and linear and branched alkyl groups comprising from 1 to 4 carbon atoms, optionally comprising at least one heteroatom chosen from O, N, S and P, and wherein the alkyl groups are optionally substituted by at least one substituent chosen from hydroxyl group, halogen atoms chosen from Cl, Br, I and F, and Si;
  acrylates with the formula $CH_2$=CH—$COOR_5$, wherein $R_5$ is chosen from tert-butyl groups, $C_3$-$C_8$ cycloalkyl groups; $C_6$-$C_{20}$ aryl groups; $C_7$-$C_{30}$ aralkyl groups ($C_1$-$C_4$ alkyl groups); heterocyclic groups comprising from 4 to 12 chain members comprising at least one heteroatom chosen from O, N, and S; heterocyclylalkyl groups ($C_1$-$C_4$ alkyl); wherein the cycloalkyl, aryl, aralkyl, heterocyclic and heterocyclylalkyl groups are optionally substituted by at least one substituent chosen from hydroxyl group, halogen atoms, and linear and branched $C_1$-$C_4$ alkyl groups optionally comprising at least one heteroatom chosen from O, N, S and P, wherein the alkyl groups are optionally substituted by at least one substituent chosen from hydroxyl groups, halogen atoms chosen from Cl, Br, I and F, and Si;
  methacrylates with the formula $CH_2$=$C(CH_3)$—$COOR_6$, wherein $R_6$ is chosen from linear and branched alkyl groups comprising from 1 to 4 carbon atoms, wherein the alkyl groups are optionally substituted by at least one substituent chosen from hydroxyl group, halogen atoms chosen from Cl, Br, I and F) and Si; $C_3$-$C_8$ cycloalkyl groups; $C_6$-$C_{20}$ aryl groups; $C_7$-$C_{30}$ aralkyl groups ($C_1$-$C_4$ alkyl groups); heterocyclic groups comprising from 4 to 12 chain members comprising at least one heteroatom chosen from O, N, and S; heterocyclylalkyl groups ($C_1$-$C_4$ alkyl); wherein the cycloalkyl, aryl, aralkyl, heterocyclic and heterocyclylalkyl groups are optionally substituted by at least one substituent chosen from hydroxyl group, halogen atoms, and linear and branched alkyl groups comprising from 1 to 4 carbon atoms, optionally comprising at least one heteroatom chosen from O, N, S and P, wherein the alkyl groups are optionally substituted by at least one substituent chosen from hydroxyl group and halogen atoms chosen from Cl, Br, I and F;
(meth)acrylamides with the formula: $CH_2=C(R')-CO-NR_7R_8$,
wherein $R_7$ and $R_8$, which may be identical or different, are chosen from hydrogen and linear and branched alkyl groups comprising from 1 to 12 carbon atoms, and R' is chosen from H and methyl.

56. The composition according to claim 55, wherein the heterocyclylalkyl groups ($C_1$-$C_4$ alkyl) are chosen from furfuryl groups.

57. The composition according to claim 55, wherein the linear and branched alkyl groups comprising from 1 to 4 carbon atoms, are chosen from methyl, ethyl, propyl and isobutyl groups.

58. The composition according to claim 55, wherein the linear or branched alkyl groups comprising from 1 to 12 carbon atoms are chosen from n-butyl, t-butyl, isopropyl, isohexyl, isooctyl, and isononyl groups.

59. The composition according to claim 1, wherein the at least one gradient copolymer further comprises at least one additional monomeric residue, said at least one additional monomeric residue resulting for at least one monomer which is capable of forming a homopolymer with a Tg greater than or equal to 20° C., wherein the at least one monomer is chosen from:
furfuryl, isobornyl, tert-butyl, tert-butylcyclohexyl and tert-butylbenzyl acrylates;
methyl, n-butyl, ethyl and isobutyl methacrylates,
styrene, styrene sulphonates;
vinyl acetates and vinylcyclohexanes.

60. The composition according to claim 1, wherein the at least one gradient copolymer is present in an amount ranging from 0.1 to 60% by weight, relative to the total weight of the composition.

61. The composition according to claim 60, wherein the at least gradient copolymer is present in an amount ranging from 0.5% to 40% by weight, relative to the total weight of the composition.

62. The composition according to claim 61, wherein the at least one gradient copolymer is present in an amount ranging from 1% to 35% by weight, relative to the total weight of the composition.

63. The composition according to claim 62, wherein the at least one gradient copolymer is present in an amount ranging from 5% to 30% by weight, relative to the total weight of the composition.

64. The composition according to claim 1, wherein the at least one gradient copolymer is present in dissolved form or else in the form of an aqueous or organic dispersion.

65. The composition according to claim 64, wherein the dissolved form is present in water or an organic solvent.

66. The composition according to claim 1, comprising at least one additional constituent chosen from water; hydrophilic and lipophilic organic solvents; waxes of animal, vegetable, mineral and synthetic origin; pasty fats and gums of animal, vegetable, mineral and synthetic origin; hydrocarbon oils of animal, vegetable, mineral and synthetic origin; hydroxylated esters; polyol esters; alcohols comprising from 12 to 26 carbon atoms; fluorinated oils partially hydrocarbonized and/or siliconized; silicone oils; ketones that are liquid at room temperature; propyleneglycol ethers that are liquid at room temperature; esters comprising from 3 to 8 carbon atoms; ethers that are liquid at room temperature; alkanes that are liquid at room temperature; aromatic cyclic compounds that are liquid at room temperature; aldehydes that are liquid at room temperature; water-soluble colorants; liposoluble colorants; pulverulent colouring matter; fillers; film-forming polymers; vitamins; thickening agents; gelling agents; trace elements; softeners; sequestering agents; perfumes; alkalizing and acidifying agents; preservatives; sun filters; surfactants; antioxidants; agents for preventing hair loss; anti-filming agents; propellants; and ceramides.

67. The composition according to claim 66, wherein said silicone oils are chosen from oils that are volatile and non-volatile, linear and cyclic, liquid and pasty at room temperature, and optionally comprising phenyl groups, such as polymethylsiloxanes (PDMS), 68. The composition according to claim 1, wherein the composition is in the form chosen from suspensions, dispersions, solutions, gels, emulsions, creams, pastes, foams, dispersions of vesicles, biphase and multiphase lotions, sprays, and powders.

69. The composition according to claim 68, wherein said emulsions are chosen from oil-in-water (O/W) emulsions, water-in-oil (W/O) emulsions, and multiple emulsions (W/O/W or polyol/O/W or O/W/O).

70. The composition according the claim 68, wherein said dispersions of vesicles are chosen from ionic and non ionic lipids.

71. The composition according to claim 68, wherein said pastes are chosen from flexible pastes.

72. The composition according to claim 1, wherein the cosmetic or dermatological composition is chosen from, make-up compositions; make-up products for the body; make-up products for the hair; compositions for protection and care of the skin, of the face, of the neck, of the hands and of the body; sun-protection and artificial tanning compositions; and hair-care products.

73. The composition according to claim 72, wherein the make-up compositions are chosen from products for the complexion; products for the lips; anti-ring products; blushers; mascaras; eyeliners; products for the eyebrows, lip and eye pencils; and products for the nails.

74. The composition according to claim 73, wherein the make-up products for the complexion are chosen from foundations, blushers and eyeshadows.

75. The composition according to claim 73, wherein the products for the lips are chosen from lipsticks and lip-care products.

76. The composition according to claim 73, wherein the products for the nails are chosen from nail varnishes and nail-care products.

77. The composition according to claim 72, wherein the compositions for protection and care of the skin, of the face, of the neck, of the hands and of the body are chosen from anti-wrinkle and anti-fatigue compositions that are able to give the skin a fresh appearance, moisturizing compositions, and treatment compositions.

78. The composition according to claim 72, wherein the hair-care products are chosen from hairdressing and hair styling, shampoo, gel, setting lotion, brushing lotion, fixing, and styling compositions.

79. The composition according to claim 78, wherein the styling compositions are chosen from lacquers and sprays.

80. A cosmetic or dermatological method for treating keratinous substances comprising applying to the keratinous substances a cosmetic or dermatological composition comprising at least one gradient copolymer comprising at least two different monomeric residues, wherein at least one monomeric residue is a hydrophilic monomeric residue, which is present in an amount ranging from 2% to 70% by weight, relative to the total weight of the copolymer, chosen from residues of:

derivatives of $C_1$-$C_4$ aminoalkyl (meth)acrylates $C_1$-$C_4$ N,N-dialkyl(meth)acrylamides and $C_1$-$C_4$ N,N-dialkyl$C_1$-$C_6$aminoalkyl(meth)acrylamides,
C1-C8 dialkyldiallylamines;
vinylamines;
vinyl pyridines;
acid salts thereof and quaternized forms thereof;
ethylenic carboxylic acids;
carboxylic anhydrides comprising at least one vinyl bond;
ethylenic sulphonic acids and their salts;
vinyl benzoic acids, vinylphosphonic acids and their salts;
potassium salts of acryloyloxy-3-sulphopropyl, and the compounds of formula $CH_2$=$CHCOOCH_2OCH_2(OH)CH_2SO_3^-Na^+$;
amides of unsaturated carboxylic acids;
hydroxyalkyl (meth)acrylates;
(meth)acrylates of polyethylene glycol (5 to 100 EO) and of glycol, which may be additionally substituted on their terminal function by at least one group chosen from alkyl, phosphate, phosphonate and sulphonate groups;
alkoxyalkyl (meth)acrylates;
(meth)acrylates of polysaccharides;
vinylam ides;
vinyl ethers;
methacrylamidopropoxytrimethylammoniumbetaines;
N,N-dimethyl-N-methacryloxyethyl-N-(3-sulphopropyl) ammoniumbetaines,
3-methacryloylethoxycarbonylpyridiniums;
a compound of formula:

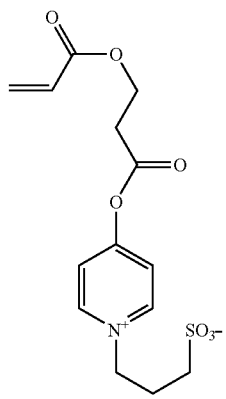

and 4-vinylpyridiniumsulphopropylbetaine of formula:

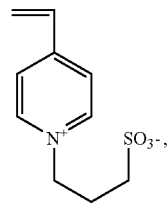

and
wherein at least one other monomeric residue results from at least one monomer which is capable of forming a homopolymer with a Tg less than or equal to 20° C., and which is present in an amount ranging from 10% to 90% by weight, relative to the total weight of the co polymer, the at least one monomer chosen from:
ethylenic hydrocarbons comprising from 2 to 10 carbons;
acrylates with the formula $CH_2$=$CHCOOR_1$, wherein $R_1$ is chosen from saturated and unsaturated hydrocarbon groups. comprising from 1 to 12 carbons, which may be linear and branched with the exception of the tert-butyl group, optionally comprising at least one heteroatom chosen from O, N, S, and Si, wherein the alkyl groups are optionally substituted by at least one substituent chosen from hydroxyl groups and halogen atoms chosen from Cl, Br, I and F;
$R_1$ can also be chosen from groups of formula: (R")x-$(OC_2H_4)_n$—OR', wherein x is an integer chosen from 0 and 1, R" is chosen from saturated and unsaturated, linear and branched hydrocarbon groups, comprising from 1 to 12 carbon atoms, n is an integer chosen from 5 to 100 and R' is chosen from H and $CH_3$;
methacrylates with formula: $CH_2$=$C(CH_3)$—$COOR_2$,
wherein $R_2$ is chosen from saturated and unsaturated, linear and branched, hydrocarbon groups, comprising from 3 to 12 carbon atoms, optionally comprising at least one heteroatom chosen from O, N, S and Si, wherein the alkyl groups are optionally substituted by at least one substituent chosen from hydroxyl groups and halogen atoms chosen from Cl, Br, I, and F; $R_2$ is also chosen from groups of formula: —(R")x-$(OC_2H_4)_n$—OR', wherein x is an integer chosen from 0 and 1, R" is chosen from saturated and unsaturated, linear and branched, hydrocarbon groups comprising from 1 to 12 carbon atoms, n is an integer chosen from 5 to 100, and R' is chosen from H and $CH_3$;
N- and N,N-substituted derivatives of amides of $C_{1-12}$ unsaturated carboxylic acids;
vinyl esters of formula: $R_3$—CO—O—CH=$CH_2$ wherein $R_3$ is chosen from linear and branched alkyl groups comprising from 2 to 12 carbon atoms; and
vinyl alkyl ethers comprising from 1 to 12 carbon atoms,
wherein the at least one gradient copolymer exhibits a mass polydispersity index (Ip) less than or equal to 2.5.

* * * * *

UNITED STATES PATENT AND TRADEMARK OFFICE
CERTIFICATE OF CORRECTION

PATENT NO. : 7,632,873 B2
APPLICATION NO. : 10/734301
DATED : December 15, 2009
INVENTOR(S) : Nathalie Mougin It is certified that error appears in the above-identified patent and that said Letters Patent is hereby corrected as shown below:

On Title page, item (75), "Nathaie" should read --Nathalie--.

In claim 1, column 25, line 41, "C1-C8" should read --$C_1$-$C_8$--.

In claim 1, column 25, lines 50-51, "$CH_2=CHCOOCH_2OCH_2(OH)CH_2SO_3^-Na^+$:" should read --$CH_2=CHCOOCH_2OCH_2(OH)CH_2SO_3^-Na^+$;--.

In claim 8, column 27, line 31, "according claim" should read --according to claim--.

In claim 14, column 27, line 57, "1 .2" should read --1.2--.

In claim 39, column 29, line 9, "according the claim" should read --according to claim--.

In claim 40, column 29, line 12, "according the claim" should read --according to claim--.

In claim 43, column 29, line 20, "according the claim" should read --according to claim--.

In claim 55, column 30, line 57, "and F)" should read --and F,--.

In claim 59, column 31, line 24, "resulting for at" should read --resulting from at--.

In claim 70, column 32, line 23, "according the claim" should read --according to claim--.

In claim 80, column 33, lines 11-12, "$C_1$-$C_4$ N,N-dialkyl$C_1$-$C_6$aminoalkyl(meth)acrylamides," should read --$C_1$-$C_4$ N,N-dialkyl$C_1$-$C_6$aminoalkyl(meth)acrylamides,--.

In claim 80, column 33, line 13, "C1-C8" should read --$C_1$-$C_8$--.

In claim 80, column 33, lines 22-23, "$CH_2=CHCOOCH_2OCH_2(OH)CH_2SO_3^-Na^+$:" should read --$CH_2=CHCOOCH_2OCH_2(OH)CH_2SO_3^-Na^+$;--.

In claim 80, column 33, line 32, "vinylam ides;" should read --vinylamides;--.

CERTIFICATE OF CORRECTION (continued)
U.S. Pat. No. 7,632,873 B2

In claim 80, column 34, line 18, "co polymer," should read --copolymer--.

In claim 80, column 34, line 23, "groups." should read --groups,--.

Signed and Sealed this

Thirtieth Day of March, 2010

David J. Kappos
*Director of the United States Patent and Trademark Office*